(12) United States Patent
Drew et al.

(10) Patent No.: US 7,764,988 B2
(45) Date of Patent: Jul. 27, 2010

(54) FLEXIBLE MEMORY MANAGEMENT SCHEME FOR LOOP RECORDING IN AN IMPLANTABLE DEVICE

(75) Inventors: Touby A. Drew, Minneapolis, MN (US); David L. Carlson, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 230 days.

(21) Appl. No.: 11/380,590

(22) Filed: Apr. 27, 2006

(65) Prior Publication Data
US 2007/0255147 A1 Nov. 1, 2007

(51) Int. Cl.
*A61B 5/0432* (2006.01)
(52) U.S. Cl. .................. 600/509; 600/523; 600/544
(58) Field of Classification Search ............. 600/523, 600/524, 544, 509, 515; 607/18
See application file for complete search history.

(56) References Cited

U.S. PATENT DOCUMENTS

| | | | |
|---|---|---|---|
| 3,958,563 A | 5/1976 | Fernandez | |
| 4,374,382 A | 2/1983 | Markowitz | |
| 4,485,813 A | 12/1984 | Anderson | |
| 4,556,063 A | 12/1985 | Thompson | |
| 4,567,892 A | 2/1986 | Plicchi | |
| 4,583,553 A | 4/1986 | Shah | |
| 4,596,251 A | 6/1986 | Plicchi | |
| 4,903,701 A | 2/1990 | Moore | |
| 5,007,431 A | 4/1991 | Donehoo, III | |
| 5,052,388 A | 10/1991 | Sivula | |
| 5,127,404 A | 7/1992 | Wyborny | |
| 5,168,759 A | 12/1992 | Bowman | |
| 5,285,792 A | 2/1994 | Sjoquist | |
| 5,312,446 A | 5/1994 | Holschbach | |
| 5,336,244 A | 8/1994 | Weijand | |
| 5,354,318 A | 10/1994 | Taepke | |
| 5,409,009 A | 4/1995 | Olson | |
| 5,518,001 A | 5/1996 | Snell | |
| 5,554,177 A | 9/1996 | Kieval | |
| 5,730,143 A * | 3/1998 | Schwarzberg | 600/523 |
| 5,732,708 A * | 3/1998 | Nau et al. | 600/523 |
| 5,752,976 A | 5/1998 | Duffin | |
| 5,782,891 A | 7/1998 | Hassler | |
| 5,785,660 A * | 7/1998 | van Lake et al. | 600/523 |
| 5,908,392 A * | 6/1999 | Wilson et al. | 600/509 |
| 5,944,745 A | 8/1999 | Rueter | |

(Continued)

FOREIGN PATENT DOCUMENTS

JP 2004254930 9/2004

(Continued)

OTHER PUBLICATIONS

International Search Report and Written Opinion, Feb. 5, 2008.

(Continued)

*Primary Examiner*—Carl H Layno
*Assistant Examiner*—Gary A Porter, Jr.
(74) *Attorney, Agent, or Firm*—Banner & Witcoff, Ltd.

(57) ABSTRACT

A method and apparatus is provided for handling multiple recordings that result from events in a limited memory device. The events may include various automatic and manual triggers. The method provides a mechanism for storing different configurations of data, associated with different events.

17 Claims, 19 Drawing Sheets

U.S. PATENT DOCUMENTS

| | | | |
|---|---|---|---|
| 5,987,352 | A | 11/1999 | Klein |
| 5,995,868 | A | 11/1999 | Dorfmeister |
| 6,016,449 | A | 1/2000 | Eischell |
| 6,067,473 | A | 5/2000 | Greeninger |
| 6,128,538 | A | 10/2000 | Fischell |
| 6,200,265 | B1 | 3/2001 | Walsh |
| 6,227,203 | B1 | 5/2001 | Rise |
| 6,360,122 | B1 | 3/2002 | Fischell |
| 6,427,086 | B1 | 7/2002 | Fischell |
| 6,496,715 | B1 | 12/2002 | Lee |
| 6,505,067 | B1 | 1/2003 | Lee |
| 6,512,940 | B1 | 1/2003 | Brabec |
| 6,522,915 | B1 | 2/2003 | Ceballos |
| 6,526,314 | B1 * | 2/2003 | Eberle et al. ................ 600/523 |
| 6,549,804 | B1 | 4/2003 | Osorio |
| 6,589,187 | B1 | 7/2003 | Dirnberger et al. |
| 6,599,242 | B1 | 7/2003 | Combs et al. |
| 6,664,729 | B2 | 12/2003 | Elledge |
| 6,778,859 | B2 * | 8/2004 | Graindorge ................... 607/59 |
| 6,823,210 | B2 * | 11/2004 | Eberle et al. ................ 600/523 |
| 7,130,678 | B2 * | 10/2006 | Ritscher et al. ............. 600/523 |
| 7,447,544 | B1 * | 11/2008 | Kroll ............................ 607/9 |
| 7,484,129 | B1 * | 1/2009 | Varrichio ..................... 714/42 |
| 2004/0138536 | A1 | 7/2004 | Frei |
| 2004/0167417 | A1 | 8/2004 | Schulhauser et al. |
| 2004/0215270 | A1 * | 10/2004 | Ritscher et al. ............... 607/27 |
| 2004/0230105 | A1 | 11/2004 | Geva et al. |
| 2005/0081847 | A1 | 4/2005 | Lee |
| 2005/0171448 | A1 * | 8/2005 | Korzinov et al. ............ 600/515 |
| 2005/0203366 | A1 | 9/2005 | Donoghue |
| 2006/0058850 | A1 * | 3/2006 | Kramer et al. ................ 607/18 |
| 2006/0095091 | A1 * | 5/2006 | Drew ........................... 607/59 |
| 2006/0287691 | A1 * | 12/2006 | Drew ........................... 607/59 |

FOREIGN PATENT DOCUMENTS

WO  2004/023983  3/2004

OTHER PUBLICATIONS

International Preliminary Report and Written Opinion for PCT/US2007/006517 mailed Nov. 6, 2008.

* cited by examiner

FLEXIBLE MEMORY MANAGEMENT SCHEME FOR LOOP RECORDING IN AN IMPLANTABLE DEVICE

FIELD OF THE INVENTION

The invention relates to techniques for selecting, storing and reporting data associated with physiologic signals that may be further associated with a neurological event.

BACKGROUND

Nervous system disorders affect millions of people, causing death and a degradation of life. Nervous system disorders include disorders of the central nervous system, peripheral nervous system, and mental health and psychiatric disorders. Such disorders include, for example without limitation, epilepsy, Parkinson's disease, essential tremor, dystonia, headache, and multiple sclerosis (MS). Additionally, mental health disorders and psychiatric disorders also include, but are not limited to, anxiety (such as general anxiety disorder, panic disorder, phobias, post traumatic stress disorder (PTSD), and obsessive compulsive disorder (OCD)), mood disorders (such as major depression, bipolar depression, and dysthymic disorder), sleep disorders (narcolepsy), obesity, and anorexia.

As an example, epilepsy is a prevalent serious neurological disease across all ages. Epilepsy is a group of neurological conditions in which a person has or is predisposed to recurrent seizures. A seizure is a clinical manifestation resulting from excessive, hypersynchronous, abnormal electrical or neuronal activity in the brain. (A neurological event is an activity that is indicative of a nervous system disorder. A seizure is a type of a neurological event.) This electrical excitability of the brain may be likened to an intermittent electrical overload that manifests with sudden, recurrent, and transient changes of mental function, sensations, perceptions, and/or involuntary body movement. Because seizures can be unpredictable, epilepsy affects a person's employability, psychosocial life, and ability to operate vehicles or power equipment. It is a disorder that occurs in all age groups, socioeconomic classes, cultures, and countries. In developed countries, the age-adjusted incidence of recurrent unprovoked seizures ranges from 24/100,000 to 53/100,000 person-years and may be even higher in developing countries. In developed countries, age specific incidence is highest during the first few months of life and again after age 70. The age-adjusted prevalence of epilepsy is 5 to 8 per 1,000 (0.5% to 0.8%) in countries where statistics are available. In the United States alone, epilepsy and seizures affect 2.3 million Americans, with approximately 181,000 new cases occurring each year. It is estimated that 10% of Americans will experience a seizure in their lifetimes, and 3% will develop epilepsy by age 75.

There are various approaches in treating nervous system disorders. Treatment therapies can include any number of possible modalities alone or in combination including, for example, electrical stimulation, magnetic stimulation, drug infusion, and/or brain temperature control. Each of these treatment modalities can be operated using closed-loop feedback control. Such closed-loop feedback control techniques receive from a monitoring element a neurological signal that carries information about a symptom or a condition or a nervous system disorder. Such a neurological signal can include, for example, electrical signals (such as EEG, ECoG, and/or EKG), chemical signals, other biological signals (such as change in quantity of neurotransmitters), temperature signals, pressure signals (such as blood pressure, intracranial pressure or cardiac pressure), respiration signals, heart rate signals, pH-level signals, and nerve signals (such as cuff electrodes on a peripheral nerve). Monitoring elements can include, for example, recording electrodes or various types of sensors.

For example, U.S. Pat. No. 5,995,868 discloses a system for the prediction, rapid detection, warning, prevention, or control of changes in activity states in the brain of a patient. Use of such a closed-loop feed back system for treatment of a nervous system disorder may provide significant advantages in that treatment can be delivered before the onset of the symptoms of the nervous system disorder.

During the operation of a medical device system, the patient is likely to experience multiple detections of the nervous system disorder. For example, in the case of seizures, the patient may have thousands of seizures over the course of a time period, but only a few of those may have behavioral manifestations. The other seizure episodes that don't exhibit behavioral manifestations are considered sub-clinical or electrographic seizures. When the medical device system monitors for seizure occurrences, however, the medical device system may detect many seizure events although only some of these events will spread to other parts of the brain such that the patient will exhibit it (e.g., convulsions, unconsciousness, etc.).

In order to effectively provide treatment therapy, an implanted device may be required to record physiologic data that is related to the disorder. However, an implanted device is typically limited by memory capacity and by battery capacity. Thus, the implanted device is limited in the amount of data that can be stored and reported.

An implanted device may store physiologic data in a data structure and manage memory allocation for the data structure. However, the memory allocation management supported by the implanted device may have deficiencies. For example, with a FIFO memory buffer if the amount of collected physiologic data exceeds the available memory space, the oldest physiologic data is lost regardless of the importance of the lost data.

It is therefore desirable to selectively store physiologic data in the limited memory space of an implanted device. The implanted device can report the most relevant data from the stored data so that the implanted device can be configured to provide efficacious treatment.

SUMMARY

The following represents a simplified summary of some embodiments of the invention in order to provide a basic understanding of various aspects of the invention. This summary is not an extensive overview of the invention nor is it intended to identify key or critical elements of the invention or to delineate the scope of the invention. Its sole purpose is to present aspects of the invention in simplified form as a prelude to the more detailed description that is presented thereafter.

In accordance with an aspect of the invention, an implantable medical device stores recordings of waveform data having specified pre-event and post-event times. The implantable medical device includes multiple sense channels to process numerous signal types. In an embodiment of the invention, various types of triggers may cause the implantable medical device to store waveform data. The triggers may include an implantable seizure detection algorithm which monitors EEG channels for seizure activity. In addition, the triggers may include cardiac arrhythmia detection logic to monitor ECG signals. Moreover, the triggers may include manual triggers operated by a patient through a patient programmer.

In accordance with another aspect of the invention, a method and apparatus is provided for handling multiple recording and their associated overlaps in a limited memory device. The method provides a mechanism for deciding what and how much information to store for events. The handling of recording includes prioritization of data stored in data blocks of a fixed buffer. A first recording includes pre-event data from a signal set that may be stored in an active buffer. The active buffer may be a circular buffer. Upon detection of a first event, pre-event data may be copied into a data block having lowest priority data. Post-event data associated with the first event may also be saved in the data block having the pre-event data of the first event.

In a further aspect of the invention, a first event associated with brain activity may be detected. Based on the detection a recording may be initiated. The recording may include a pre-event time and post-event time. In addition, a second event associated with heart activity may also be detected. A determination may be made whether to initiate a second recording for the second event based on loop overlap and the status of the post-event recording associated with the first loop recording.

DETAILED DESCRIPTION OF THE INVENTION

Figure 1:
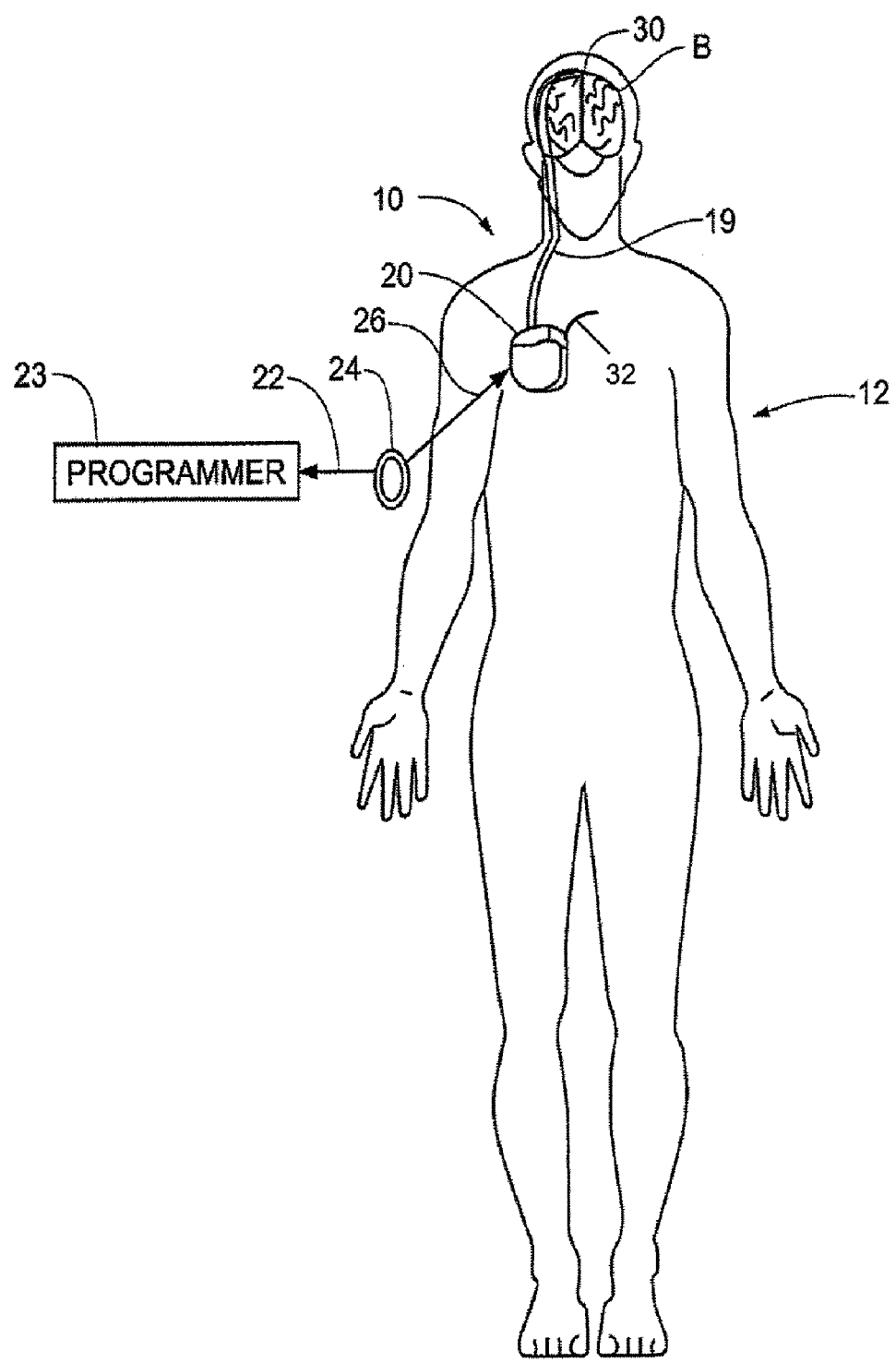
FIG. 1 is a schematic view of a medical device implanted in a patient that monitors cardiac and nervous system disorders in accordance with an aspect of the invention.

The following description discloses techniques for selecting, storing and reporting data associated with physiologic signals that may be further associated with a neurological event. These techniques are suitable for use within any implantable medical device system. For example, an implantable medical device may consist of ECG and EEG inputs. The monitoring device may monitor the neural or cardiac inputs in various combinations.

In an embodiment, the invention may be implemented within an implantable neurostimulator system, however, as already discussed, those skilled in the art will appreciate that the techniques disclosed herein may be implemented generally within any implantable medical device system having monitoring capabilities of physiological conditions of the patient including, but not limited to, implantable drug delivery systems, implantable systems providing stimulation and drug delivery, pacemaker systems, defibrillator systems, cochlear implant systems, and implantable diagnostic system for detecting bodily conditions, including those in organs like the brain and/or the heart. The implantable medical device may provide therapeutic treatment to neural tissue in any number of locations in the body including, for example, the brain (which includes the brain stem), the vagus nerve, the spinal cord, peripheral nerves, etc. The treatment therapies can include any number of possible modalities alone or in combination including, for example, electrical stimulation, magnetic stimulation, drug infusion, brain temperature control, and/or any combination thereof.

In addition, aspects of the invention may be embodied in various forms to analyze and treat nervous system and other disorders, namely disorders of the central nervous system, peripheral nervous system, and mental health and psychiatric disorders. Such disorders include, for example without limitation, epilepsy, Sudden Unexpected Death in Epilepsy Patients (SUDEP), Parkinson's disease, essential tremor, dystonia, multiple sclerosis (MS), anxiety (such as general anxiety, panic, phobias, post traumatic stress disorder (PTSD), and obsessive compulsive disorder (OCD)), mood disorders (such as major depression, bipolar depression, and dysthymic disorder), sleep disorders (narcolepsy), obesity, tinnitus, stroke, traumatic brain injury, Alzheimer's, and anorexia.

The physiologic signals that are selected, stored and reported in accordance with various aspects of the invention may include any number of sensed signals. Such physiological signals can include, for example, electrical signals (such as EEG, ECoG and/or EKG), chemical signals, biological signals (such as change in quantity of neurotransmitters), temperature signals, pressure signals (such as blood pressure, intracranial pressure or cardiac pressure), respiration signals, heart rate signals, pH-level signals, activity signals (e.g., detected by an accelerometer), and/or peripheral nerve signals (cuff electrodes on a peripheral nerve). Such physiological signals may be recorded using one or more monitoring elements such as monitoring electrodes or sensors. For example, U.S. Pat. No. 6,227,203 provides examples of various types of sensors that may be used to detect a symptom or a condition or a nervous system disorder and responsively generate a neurological signal. In addition, various types of physiologic activities may be sensing including, for example, brain, heart and/or respiration.

As discussed, the techniques disclosed herein are suitable for use within any implantable medical device system that receives signals associated with the physiological conditions being sensed, a memory component, and a processing component (logic or software) that stores data records in data structures.

In an aspect of the invention, the medical device monitors cardiac (ECG) and neural (EEG) signals and records these signals as discussed herein. Real-time analysis of the ECG signal evaluates rate disturbances (e.g., bradycardia; tachycardia; asystole) as well as any indications of cardiac ischemia (e.g., ST segment changes; T wave inversion, etc).

Abnormalities detected during real-time analysis may lead to an immediate patient alert, which can be audible (beeps, buzzers, tones, spoken voice, etc.), light, tactile, or other means. Manual indication of a seizure or other event may be achieved through an external programmer device. The patient (or caregiver) may push a button on the external programmer device, while communicating with the implanted device. This will provide a marker and will initiate a recording, as discussed herein, of the sensed data (for example, in the event the patient is experiencing a neurological event).

In assessing the risk of SUDEP, for example, prolonged ECG recordings may be possible (e.g., recording all data during sleep since the incidence of SUDEP is highest in patients during sleep). Post-processing of the signal can occur in the implanted device, the patient's external device, a clinician external device, and/or another computing device.

Intermittently (e.g., every morning, once/week, following a seizure), a patient may download data from the implantable device to the patient external device (as will be discussed further herein), which may then be analyzed by the external device (and/or sent through a network to the physician) to assess any ECG abnormalities. If an abnormality is detected, the device may notify the patient/caregiver. At that time, the patient/caregiver may inform the healthcare provider of the alert to allow a full assessment of the abnormality. The clinician external device may also be capable of obtaining the data from the implanted device and conducting an analysis of the stored signals. If a potentially life-threatening abnormality is detected, the appropriate medical treatment may be prescribed (e.g., cardiac abnormality: a pacemaker, an implantable defibrillator, or a heart resynchronization device may be indicated or respiration abnormality: CPAP, patient positioning, or stimulation of respiration may be indicated).

Moreover, the implantable medical device may also monitor EEG signals from intracranially implanted leads. This may allow the implanted medical device to collect cardiovascular and neurological signals in close proximity to detected neurological events as well as notify the patient/caregiver of a prolonged event (and/or status epilepticus).

The implantable medical device may detect neurological events and analyze the peri-ictal signals and initiate loop recording.

Again, it will be appreciated that alternative embodiments of the implantable medical device may also be utilized. For example, cardiac lead(s), a sensor stub, and/or a wearable patch may be used to facilitate detection of a neurological event and the recording of data and signals pre and post event. An integrated electrode may also be used that senses ECG signals as described in U.S. Pat. No. 5,987,352. Optionally, the implantable medical device may warn/alert the patient 12 via buzzes, tones, beeps or spoken voice (as substantially described in U.S. Pat. No. 6,067,473) via a piezo-electric transducer incorporated into the housing of implantable medical device. The sound may be transmitted to the patient's inner ear.

In another embodiment, the monitor may be implanted cranially in the patient 12 (FIG. 1). In such an embodiment, the monitor may be constructed as substantially described in U.S. Pat. Nos. 5,782,891 and 6,427,086. EEG sensing may be accomplished by the use of integrated electrodes in the housing of the monitor, cranially implanted leads, and or leadless EEG sensing.

FIG. 1 illustrates an implantable system 10 including an implantable medical device 20 implanted in a patient 12. The implantable medical device 100 continuously senses and monitors one or more physiological conditions of the patient via lead 19 and monitoring/sensing elements 30 and 32 (in the embodiment, the physiological conditions are cardiac and neurological functions of patient 12). Stored diagnostic data is uplinked and evaluated by an external computing device 23 (e.g., a patient's or physician's programmer) via a 2-way telemetry, using for example, antenna 24 to relay radio frequency signals 22, 26 between implantable medical device 100 and external computing device 23. An external patient activator that may be located on external computing device 23 may optionally allow patient 12, or care provider (not shown), to manually activate the recording of diagnostic data.

Figure 2:
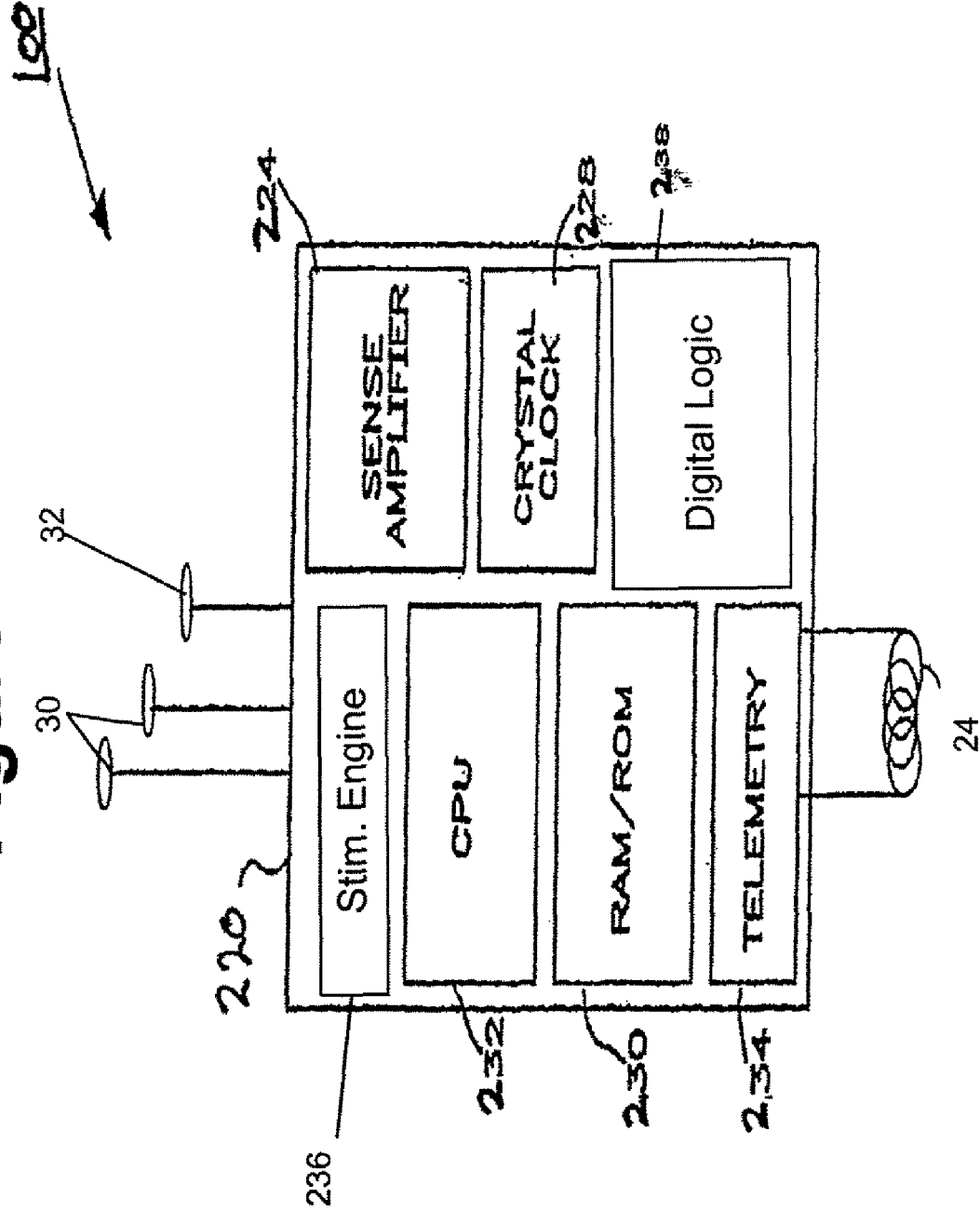
FIG. 2 is a simplified block diagram of the medical device shown in FIG. 1 in accordance with an aspect of the invention.

FIG. 2 depicts a block diagram of the electronic circuitry of implantable medical device 100 of FIG. 1 in accordance with an embodiment of the invention. Implantable medical device 100 comprises a primary control circuit 220 and may be similar in design to that disclosed in U.S. Pat. No. 5,052,388. Primary control circuit 220 includes sense amplifier circuitry 224, a crystal clock 228, a random-access memory and read-only memory (RAM/ROM) unit 230, a central processing unit (CPU) 232, digital logic circuit 238, a telemetry circuit 234, and stimulation engine circuitry 236, all of which are generally known in the art.

Implantable medical device 100 may include internal telemetry circuit 234 so that it is capable of being programmed by means of external programmer/control unit 23 via a 2-way telemetry link. External programmer/control unit 23 communicates via telemetry with implantable medical device 100 so that the programmer can transmit control commands and operational parameter values to be received by the implanted device, and so that the implanted device can communicate diagnostic and operational data to the programmer 23. For example, programmer 23 may be Models 9790 and CareLink® programmers, commercially available from Medtronic, Inc., Minneapolis, Minn. Various telemetry systems for providing the necessary communications channels between an external programming unit and an implanted device have been developed and are well known in the art. Suitable telemetry systems are disclosed, for example, in U.S. Pat. Nos. 5,127,404; 4,374,382; and 4,556,063.

Typically, telemetry systems such as those described in the above referenced patents are employed in conjunction with an external programming/processing unit. Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna 24 for receiving downlink telemetry signals and for radiating RF signals for uplink telemetry. The system is modeled as an air-core coupled transformer. An example of such a telemetry system is shown in U.S. Pat. No. 4,556,063.

In order to communicate digital data using RF telemetry, a digital encoding scheme such as is described in U.S. Pat. No. 5,127,404 can be used. In particular, a pulse interval modulation scheme may be employed for downlink telemetry, wherein the external programmer transmits a series of short RF "bursts" or pulses in which the interval between successive pulses (e.g., the interval from the trailing edge of one pulse to the trailing edge of the next) is modulated according to the data to be transmitted. For example, a shorter interval may encode a digital "0" bit while a longer interval encodes a digital "1" bit. For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen-position data frame may be defined, wherein a pulse in one of the time slots represents a unique four-bit portion of data.

Programming units such as the above-referenced Medtronic Models 9790 and CareLink® programmers typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

As previously noted, primary control circuit 220 includes central processing unit 232 which may be an off-the-shelf programmable microprocessor or microcontroller, but in an embodiment of the invention it may be a custom integrated circuit. Although specific connections between CPU 232 and other components of primary control circuit 220 are not shown in FIG. 2, it will be apparent to those of ordinary skill in the art that CPU 232 functions to control the timed operation of sense amplifier circuit 224 under control of programming stored in RAM/ROM unit 230. In addition to or as an alternative embodiment digital logic 238 may also be provided and utilized. In another alternative embodiment, a processing module that contains either a processor or digital circuitry may also be utilized. Those of ordinary skill in the art will be familiar with such an operative arrangement.

With continued reference to FIG. 2, crystal oscillator circuit 228 provides main timing clock signals to primary control circuit 220. The various components of implantable medical device 100 are powered by means of a battery (not shown), which is contained within the hermetic enclosure of implantable medical device 100. For the sake of clarity in the figures, the battery and the connections between it and the other components of implantable medical device 100 are not shown. Sense amplifier 224 is coupled to monitoring/sensing elements 30 and 32. Where cardiac intrinsic signals are sensed, they may be sensed by sense amplifier 224 as substantially described in U.S. Pat. No. 6,505,067.

Processing by CPU 232 or digital logic 238 allows detection of cardiac and neural electrical characteristics and anomalies. Upon detection of either a cardiac or neural anomaly, CPU 232 or digital logic 238, under control of firmware resident in RAM/ROM 230, will initiate recording of the appropriate diagnostic information into RAM of RAM/ROM 230 (discussed further herein), and may initiate a warning or alert to the patient, patient caregiver, or remote monitoring location.

Figure 3:
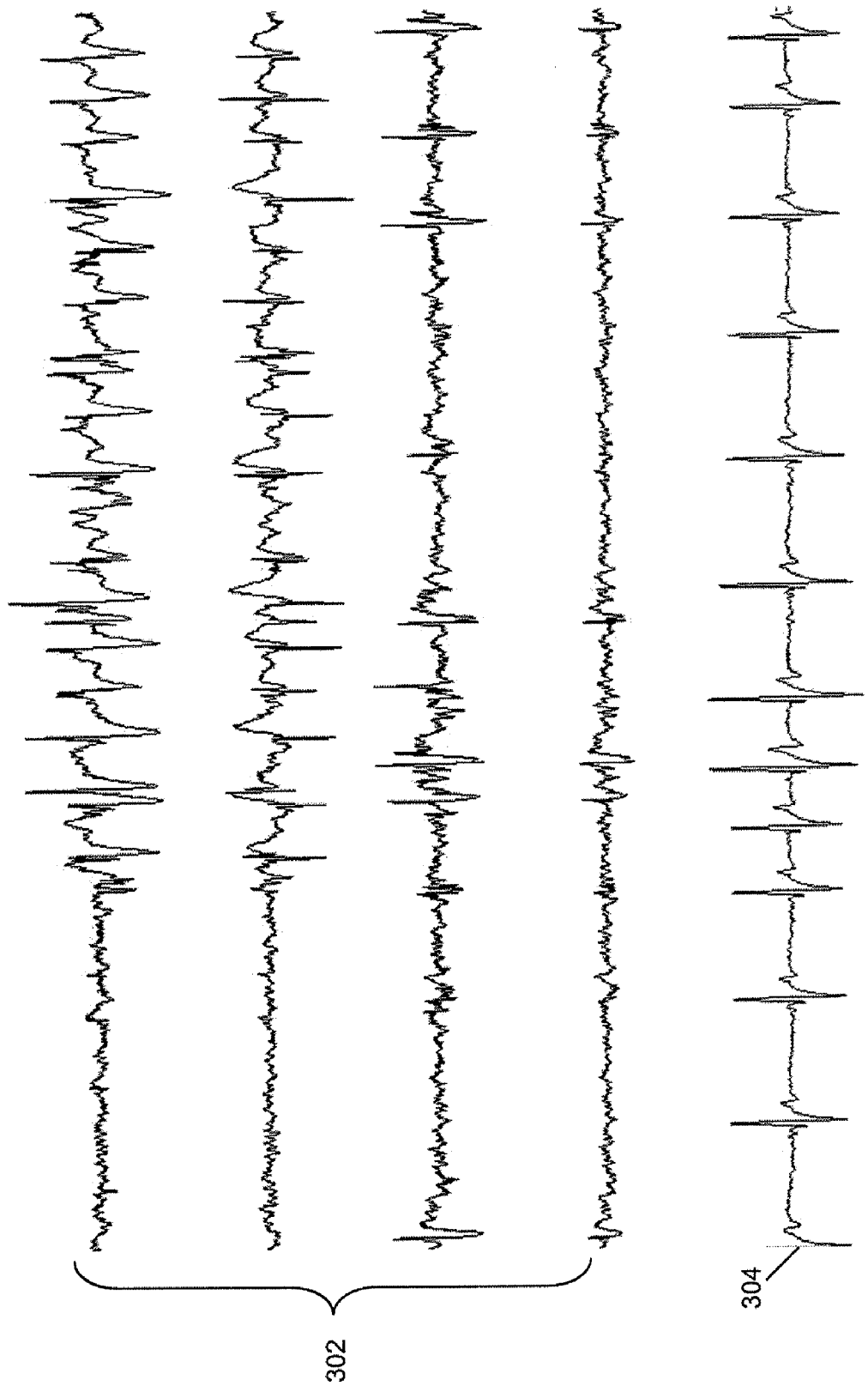
FIG. 3 is a graphical representation of various signals sensed by the medical device as shown in FIG. 1 in accordance with an aspect of the invention.

The recording of EEG and ECG signal simultaneously may allow a physician to assess the interplay between brain and cardiac signals, particularly when a seizure and/or cardiac arrhythmia are present. For example, FIG. 3 shows the interplay between EEG signals 302 and ECG signal 304. Both EEG signals 302 and the ECG signal 304 may be presented to sense amplifier 224 from monitoring elements 30 and 32. Note the amplitude variation of cardiac signals may be caused by the change in thoracic cavity pressure due to respiration (i.e., inspiration and expiration).

It will be appreciated that alternative embodiments of implantable medical device 100 may also be utilized. As discussed above, implantable medical device 100 may sense any number of physiologic conditions of the patient 12 for purposes of detecting, and storing data relating to, any number of the neurological events. For example, various lead(s) may be used to facilitate detection of a neurological event and the recording of data and signals pre and post event. For example, cardiac leads may consist of any typical lead configuration as is known in the art, such as, without limitation, right ventricular (RV) pacing or defibrillation leads, right atrial (RA) pacing or defibrillation leads, single pass RA/RV pacing or defibrillation leads, coronary sinus (CS) pacing or defibrillation leads, left ventricular pacing or defibrillation leads, pacing or defibrillation epicardial leads, subcutaneous defibrillation leads, unipolar or bipolar lead configurations, or any combinations of the above lead systems.

In another aspect of the invention, an electrode 32 located distally on a sensor stub may be used to facilitate detection of a neurological event and the recording of data and signals pre and post event. The sensor stub 32 is inserted subcutaneously in a thoracic area of the patient 12. The implantable medical device 100 may sense cardiac signals between an electrode on the distal end of the sensor stub and the implantable medical device case as described in conjunction with the embodiment shown in FIG. 5 in U.S. Pat. No. 5,987,352. In alternative embodiments of the invention, the implantable medical device 100 may also sense respiration parameters such as respiration rate, minute ventilation and apnea via measuring and analyzing the impedance variations measured from the implanted implantable medical device 100 case to the electrode located distally on the sensor stub lead as substantially described in U.S. Pat. Nos. 4,567,892 and 4,596,251.

In yet another aspect of the invention, an external wearable device such as a wearable patch, a wristwatch, or a wearable computing device may be used to continuously sense implantable medical device cardiac functions of patient 12. Optionally, a button (not shown) on the external wearable device may be activated by the patient 12 (or a caregiver) to manually activate data recording (for example, in the event the patient is experiencing a neurological event). The external wearable device may comprise an amplifier, memory, microprocessor, receiver, transmitter and other electronic components as substantially described in U.S. Pat. No. 6,200,265. In the embodiment of a wearable patch, the device may consist of a resilient substrate affixed to the patient's skin with the use of an adhesive. The substrate flexes in a complimentary manner in response to a patient's body movements providing patient comfort and wearability. The low profile patch is preferably similar in size and shape to a standard bandage, and may be attached to the patient's skin in an inconspicuous location.

As exemplified above, any number of implantable medical device systems are envisioned that may incorporate the recording and retention techniques discussed herein. For example, the monitoring may be achieved using any of the above techniques in conjunction with treatment by delivery of treatment therapy (e.g., electrical stimulation) to the brain, cardiac or respiration.

The above embodiments illustrate that the disclosed techniques may be implemented within any number of medical device systems (drug delivery, electrical stimulation, pacemaking, defibrillating, cochlear implant, and/or diagnostic) but configured to retain sensed data records in accordance with the teachings disclosed herein. In general, the implanted medical component utilizes one or more monitoring elements (e.g., electrodes or other sensors), a memory component having a plurality of data structures (and/or data structure types), a processing component (such as a CPU or digital logic) to process received data for storage in memory as disclosed herein, and a telemetry component.

Figure 4:
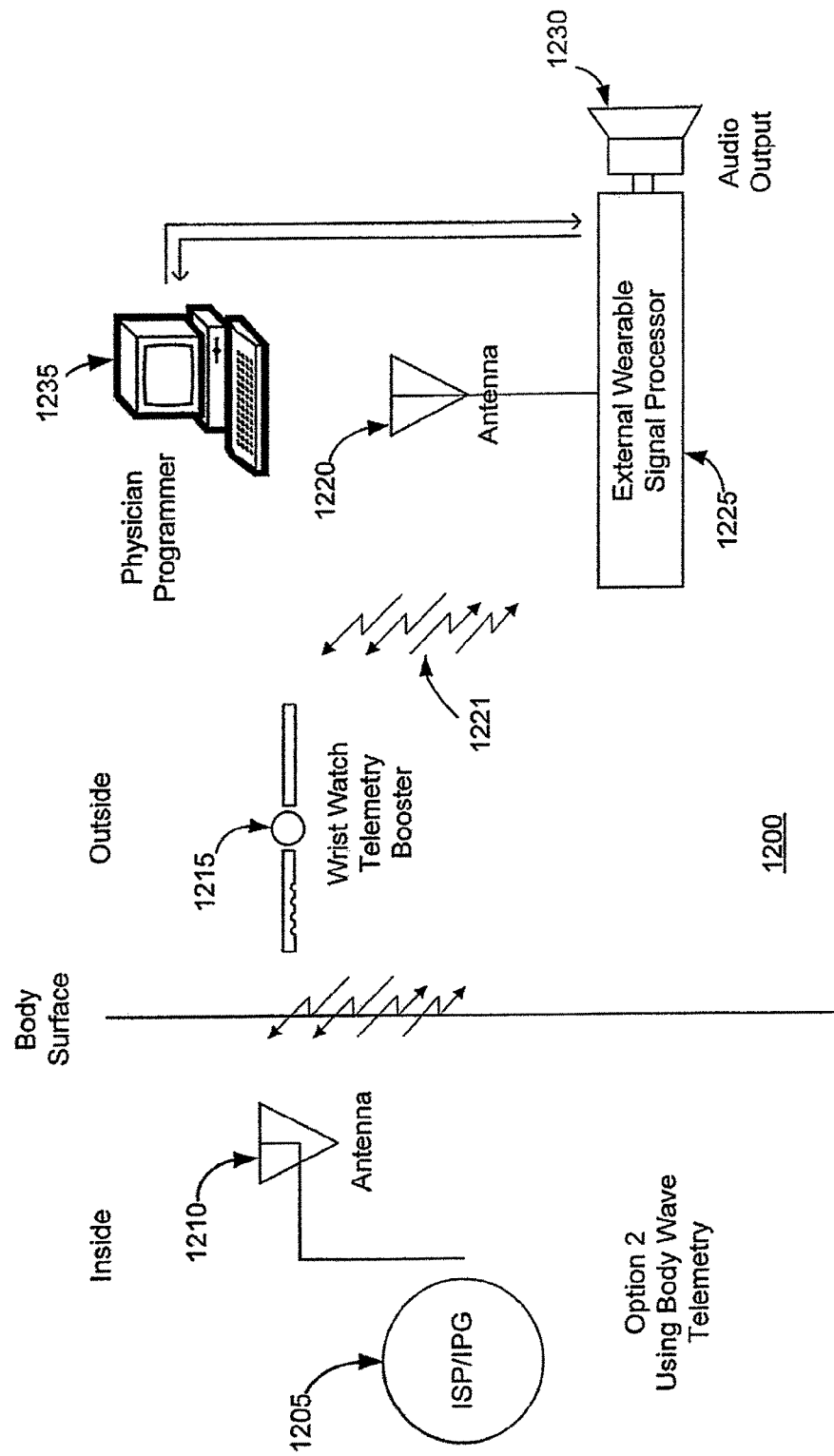
FIG. 4 shows an apparatus that supports reporting neurological data in accordance with an aspect of the invention.

FIG. 4 shows apparatus 1200 that supports reporting physiological data in accordance with an aspect of the invention. With apparatus 1200, the implanted component 1205 of the medical device system communicates with the relaying module 1215 via telemetry antenna 1210. Similarly, the external component 1225 communicates with the relaying module 1215 via antenna 1220. In the embodiment, a telemetry link 1221 between relaying module 1215 and antenna 1220 comprises a 3 MHz body wave telemetry link. To avoid interference, the relaying module 1215 may communicate with the external and implanted components using differing communication schemes. In some embodiments, the reverse direction and the forward direction of telemetry link 1221 may be associated with different frequency spectra. The relaying module 1215 thereby provides a greater range of communications between components of medical device system. For example, in the embodiment of an implanted system, an external programmer may communicate with an implanted device from a more remote location. The external programmer may be across the room and still be in communication via the relaying module 1215. With the telemetry booster stage, the use of an implanted system is more convenient to the patient, in particular at night while sleeping or when taking a shower, eliminating the need for an external device to be worn on the body.

Figure 5:
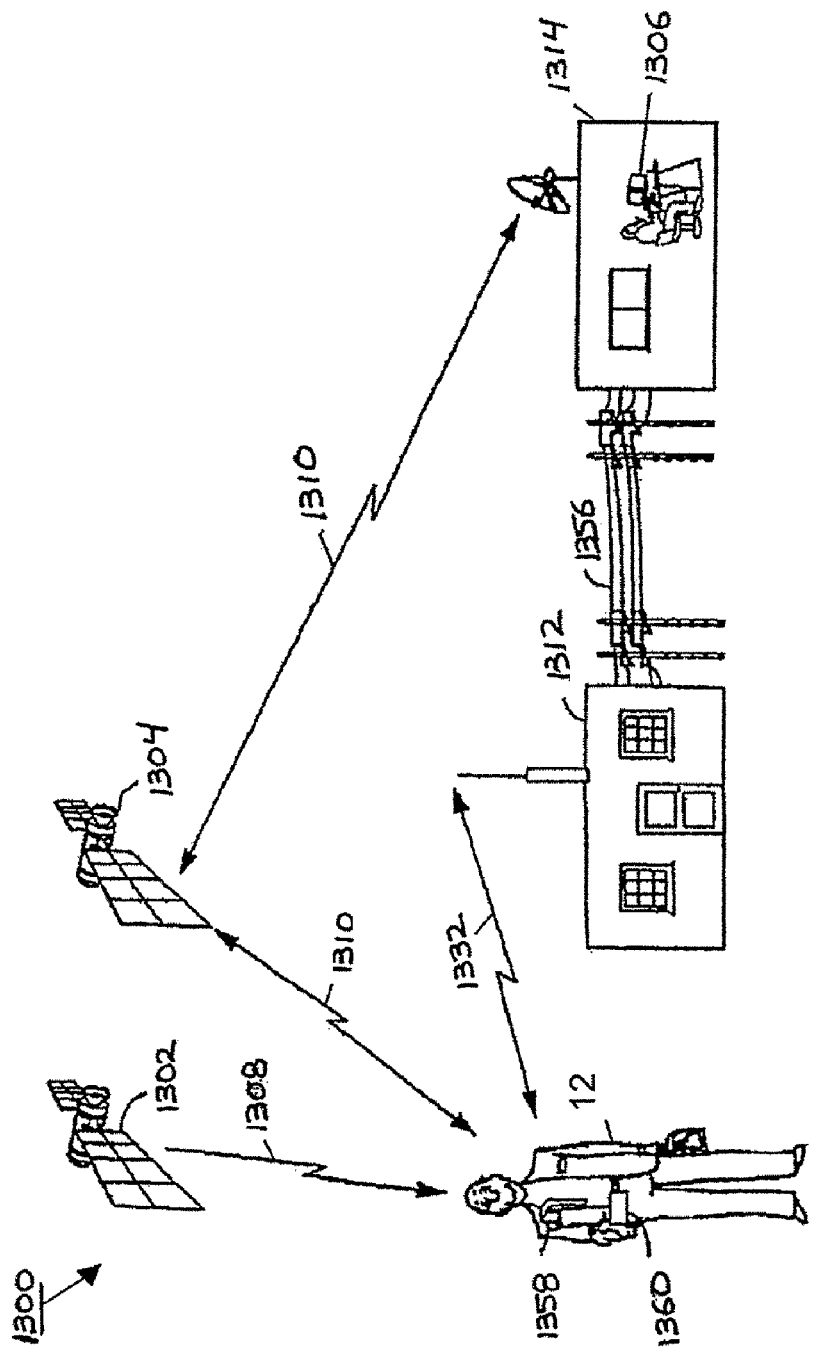
FIG. 5 is a schematic diagram of a system utilizing the above-described embodiments and allowing remote monitoring and diagnostic evaluation of at risk patients in accordance with an aspect of the invention.

As shown in FIG. 5, in an embodiment, the system allows the residential, hospital or ambulatory monitoring of at-risk patients and their implanted medical devices at any time and anywhere in the world. Medical support staff 1306 at a remote medical support center 1314 may interrogate and read telemetry from the implanted medical device and reprogram its operation while the patient 12 is at very remote or even unknown locations anywhere in the world. Two-way voice communications 1310 via satellite 1304, via cellular link 1332 or land lines 1356 with the patient 12 and data/programming communications with the implanted medical device 1358 via a belt worn transponder 1360 may be initiated by the patient 12 or the medical support staff 1306. The location of the patient 12 and the implanted medical device 1358 may be determined via GPS 1302 and link 1308 and communicated to the medical support network in an emergency. Emergency response teams can be dispatched to the determined patient location with the necessary information to prepare for treatment and provide support after arrival on the scene. See for example, U.S. Pat. No. 5,752,976.

Figure 6:
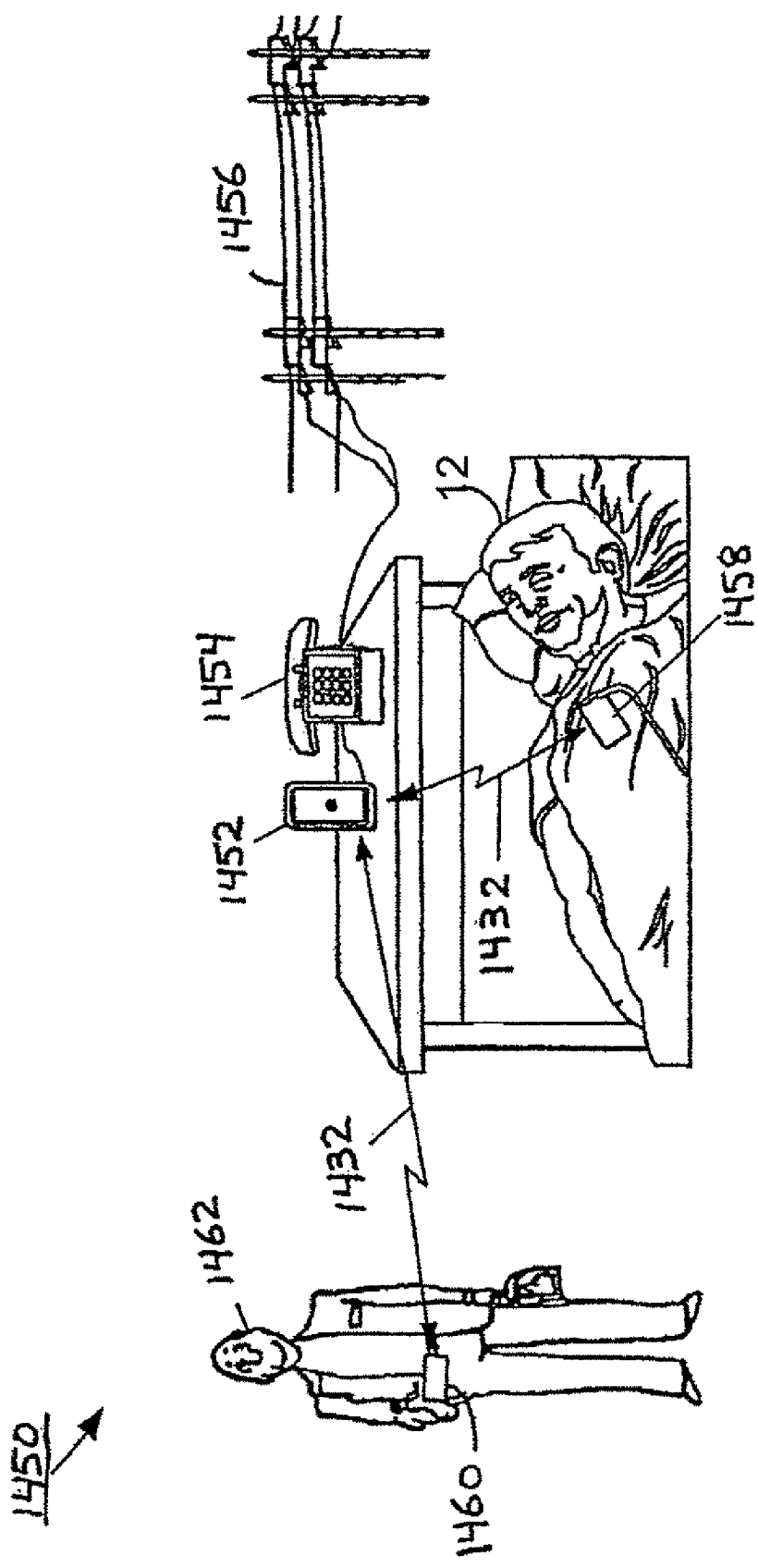
FIG. 6 is a schematic diagram of an alternative system utilizing the above-described embodiments and allowing remote monitoring and diagnostic evaluation of at risk patients in accordance with an aspect of the invention.

An alternative or addition to the remote monitoring system as described above in conjunction with FIG. 5 is shown in the system 1450 of FIG. 6, which shows a patient 12 sleeping with an implantable Monitor 1458 and/or optional therapy device as described above in connection with the above-described systems. The implantable device 1458, upon detection of a neurological event may alert a remote monitoring location via local remote box 1452 (as described in U.S. Pat. No. 5,752,976), telephone 1454 and phone lines 1456 or the patient's care provider via an RF link 1432 to a pager-sized remote monitor 1460 placed in other locations in the house or carried (i.e., belt worn) by the care provider 1462. The remote caregiver monitor 1460 may include audible buzzes/tones/beeps, vocal, light and/or vibration to alert the caregiver 1462 of patient's monitor in an alarm/alert condition. The RF link may include RF portable phone frequencies, power line RF links, HomeRF, Bluetooth, ZigBee, WIFI, MICS band (medical implant communications service), or any other interconnect methods as appropriate.

In another aspect of the invention, techniques for selecting and storing sensed physiological data in an implanted medical device for subsequent reporting to an external device are disclosed. As used herein, the term data record encompasses the sensed physiological data, summary information, or simply a pointer that references a location in memory where the sensed physiological data is stored. Thus, the concept of storage of data records in first and second data structures envisions possibilities of storage of the sensed physiological data and the storage of their associated pointers. As an example, summary information data may be stored in the first and second data structures wherein the more detailed and more space consuming waveform data (pre-detection data, post-detection data, etc.) may be stored, and pointed to, in an associated memory (such as a loop record buffer).

Mapping from entries in the first and second data structures to the waveform physiological data that is stored in the associated memory may be achieved with pointers.

Each entry in the event log may point to its corresponding waveform data, or each waveform data may point to its corresponding data in the event log. Alternatively, multi-directional pointers in an "allocation table" or "allocation data structure" may be pointed to by the priority structures. Thus, when a data record is overwritten or replaced as discussed herein, both the data record itself and its mapping to the event log may be changed/removed in the allocation structure.

In an embodiment, the implantable medical device may have a set of monitoring elements sensing brain activity and another set of monitoring element that sense a physiological activity other than the brain (e.g., heart activity such as a heart arrhythmia and/or respiratory activity). The device may then implement a detection algorithm to determine the possible onset of a possible neurological event (e.g., a seizure) based on the sensed signals from either the first or second monitoring elements. Once a neurological event is detected, data records associated with the first and second monitoring elements may be stored in memory in accordance with the teachings herein.

Alternatively or additionally, the device may initiate loop recording upon indication to do so by the patient based, for example, on a patient detecting a neurological event. In the event the patient initiates loop recording based on detection of a neurological event (wherein, however, the detection process of the implanted device has not detected the neurological event), the priority index (discussed below) for such data may be set at a higher level such that the data is stored in a memory. In the situation where the patient experiences a neurological event but the medical device has not detected the event, the physiological sensed data may be particularly important for storage and subsequent evaluation. In an exemplary embodiment, once activated by a patient, loop recording may save the data for 30 seconds before the indicated seizure and 3 minutes after the seizure. However, to allow for the fact that the patient may not mark the seizure until the seizure has ended the ECG loop recording may begin 3 to 5 minutes before the patient mark. This time period may be programmable. In another aspect of the invention, the ECG loop recording may begin before the patient mark from a time period ranging between 30 seconds to one hour. As discussed below, a subset or a composite of physiologic channels is selected from the available physiologic channels based on a selection criterion.

In an aspect of the invention, a priority index may be utilized to organize different recorded events. The priority index may be expressed as a mathematical combination of the severity level function $f(x_1, x_2, \ldots, x_n)$ and the associated factor function $g(y_1, y_2, \ldots y_m)$. For example, the priority level may be expressed as:

$$\text{priority index} = f(x_1, x_2, \ldots, x_n) + g(y_1, y_2, \ldots y_m) \qquad (\text{EQ. 1A})$$

Either $f(x_1, x_2, \ldots, x_m)$ or $g(y_1, y_2, \ldots y_m)$ may be a continuous function, a discrete-value function, a Boolean function, or a combination of the above function types. As another example, the priority level may be expressed as:

$$\text{priority index} = f(x_1, x_2, \ldots, x_n) \cdot g(y_1, y_2, \ldots y_m) \qquad (\text{EQ. 1B})$$

The priority index may be more generally expressed as a function $h(z_1, z_2)$, where $$\text{priority index} = h(f(x_1, x_2, \ldots, x_n), g(y_1, y_2, \ldots y_m)) \qquad (\text{EQ. 1C})$$

In accordance with an aspect of the invention, in response to an instruction from a clinician, an implanted device organizes stored physiological data according to the associated priority index and reports a predetermined number of data records that are deemed as having a higher priority index than the other stored data records.

The above approach may be extended to include the retention of more than one channel from a channel list sorted by relevancy as determined by a function of various factors (e.g., onset time, presence and severity of an event) as previously discussed. One may keep the most relevant physiologic channels of the channel list. For example, one may keep the three most relevant ("interesting") physiologic channels of five physiologic channels. Keeping the two or most relevant physiologic channels is referred as the "multi-max" of the channel list.

With an embodiment of the invention, the selection of physiologic channels may occur after filtering (e.g., bandpass, notch, FIR, and IIR) the physiologic channels. For example, an EEG signal may be filtered in the 10-60 Hz range to remove the bulk of the EEG energy content that may otherwise mask the ictal content. As another example, the physiologic channels may be filtered in the 180-250 Hz range in order to study "fast-ripple" events.

In another aspect of the invention, techniques for storing recording of event data in an implanted medical device for subsequent reporting and analysis are disclosed. Due to memory constraints of implantable devices, the storage of duplicative overlapping data should be avoided. As those skilled in the art will realize, a computing device with an associated computer readable-medium containing instructions for controlling the computing device may be utilized to implement the exemplary embodiments that are disclosed in this description.

In an aspect of the invention, all events are logged into an event recorder regardless of whether data specific to a particular event is saved or overwritten due to full memory.

Furthermore, in another aspect of the invention, all pre-event and post-event times may be the same for all events. However, as those skilled in the art will realize both pre-event and post-event times may be adjusted such that the total time saved for each event remains the same.

Discussed herein are techniques for storing recordings of event data in an implanted medical device for subsequent reporting and analysis. Due to memory constraints of implantable devices, the storage of duplicative overlapping data should be avoided. As those skilled in the art will realize, a computing device with an associated computer readable-medium containing instructions for controlling the computing device may be utilized to implement the exemplary embodiments that are disclosed in this description.

The computing device as described above in various embodiments may include a processor such as microprocessor or other digital logic computing hardware.

In accordance with an aspect of the invention, an implantable medical device stores loop recordings of waveform data having specified pre-event and post-event times. The implantable medical device may also include a multitude of sense channels to process numerous signal types. Overlaps as discussed below occur when the storing of data related to a second event overlaps the storing of data from a first event. Because data relating to both events may be stored redundantly, memory capacity for additional events is diminished.

In an aspect of the invention, all events may be logged into an event recorder regardless of whether data specific to a particular event is saved or overwritten due to full memory. In addition, for different events certain event characteristics such as pre-event time, post-event time, total recoding time, trigger mapping, and/or channel mask/content may be adjustable to capture various data associated with the different events.

For example, in an event such as detection of a seizure, a physician or caregiver may want to analyze data starting at two minutes before the event to and including five minutes after completion of the event. As another example, for an event such as heart arrhythmia detection, a physician or caregiver may want to record data starting at five minutes before the event to and including three minutes after completion of the event.

Figure 7:
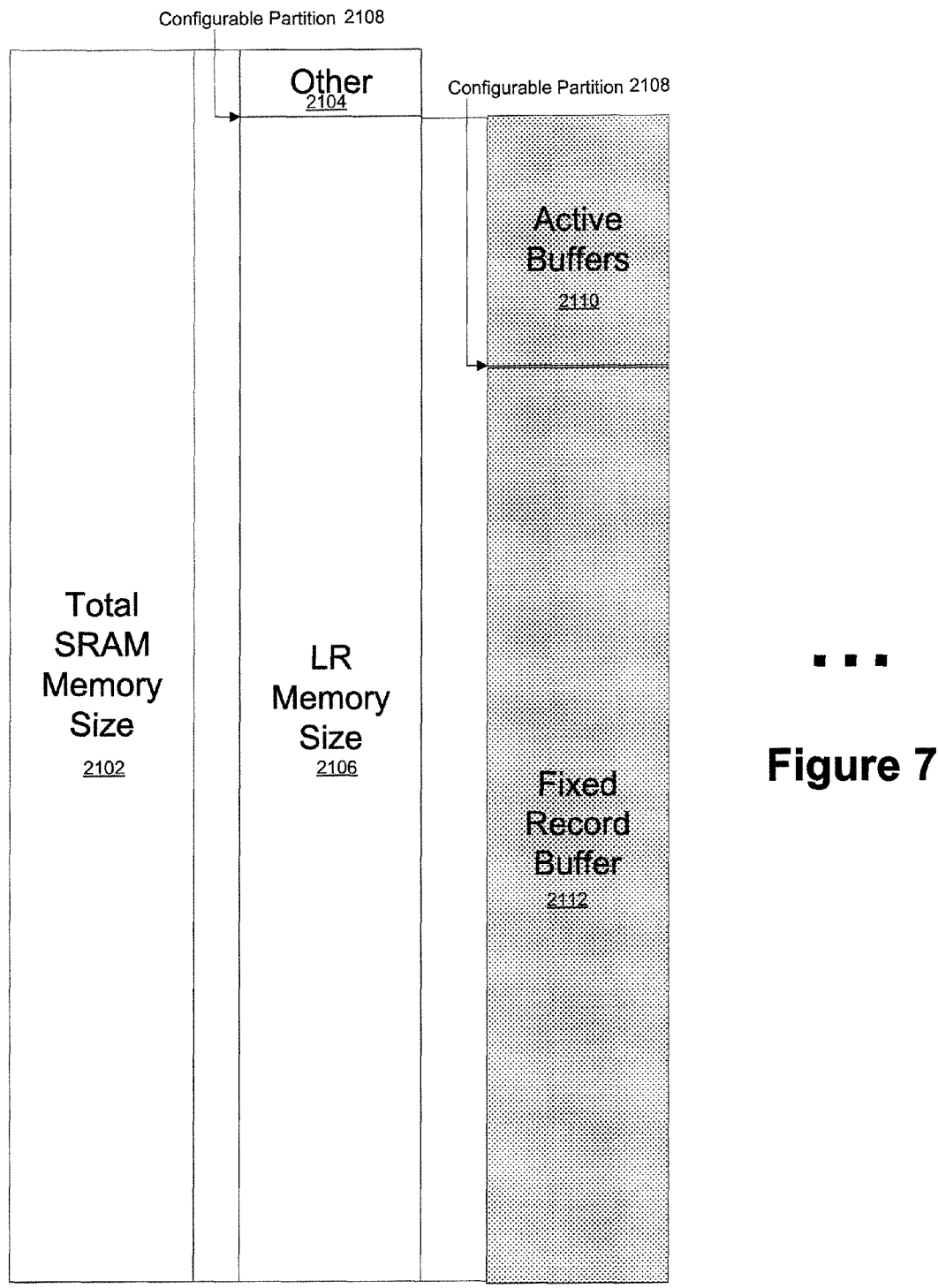
FIG. 7 illustrates a flexible memory management scheme in accordance with an aspect of the invention.

FIG. 7 illustrates a flexible memory management scheme that may be used in accordance with an aspect of the invention. In FIG. 7, memory such as SRAM 2102 may be used to store recording of various events. Those skilled in the art will realize that other forms of memory other than SRAM may be utilized in various embodiments of the invention.

Events may be triggered automatically by various algorithms or by other inputs, for example telemetry commands from a patient device. In one aspect of the invention, other inputs may include manual triggers issued by a patient. In an embodiment of the invention, various types of triggers may cause the implantable device to store waveform data. Triggers may include an implantable seizure detection algorithm which monitors EEG channels for seizure activity. In addition, triggers may include cardiac arrhythmia detection logic to monitor ECG signals.

The SRAM 2102 may have a total storage capacity of 2 MB. The 2 MB of memory may be divided up to store various types of data. For example, a certain portion of SRAM memory 2102 may be needed to store log events or "other" 2104 information for non-loop recording purposes. The remaining portion of memory may be allocated for storing waveform data or loop recordings 2106 associated with the events. As those skilled in the art will realize, a device such as an implantable device may have more or less memory than the exemplary 2 MB of memory discussed above for use in storing waveform and event data. Also, as shown in FIG. 7 the amount of memory allocated to store different types of data may be configurable 2108.

In an aspect of the invention, loop recording memory 2106 may be separated into active buffers 2110 and a fixed record buffer 2112. The active buffers 2110 as further illustrated in FIG. 8 may be circular buffers that store pre-event data. Active buffers 2110 may overwrite older data as new data is recorded. As those skilled in the art will realize, the size of active buffers 2110 may determine the number and size of recording that may be stored.

Figure 8:
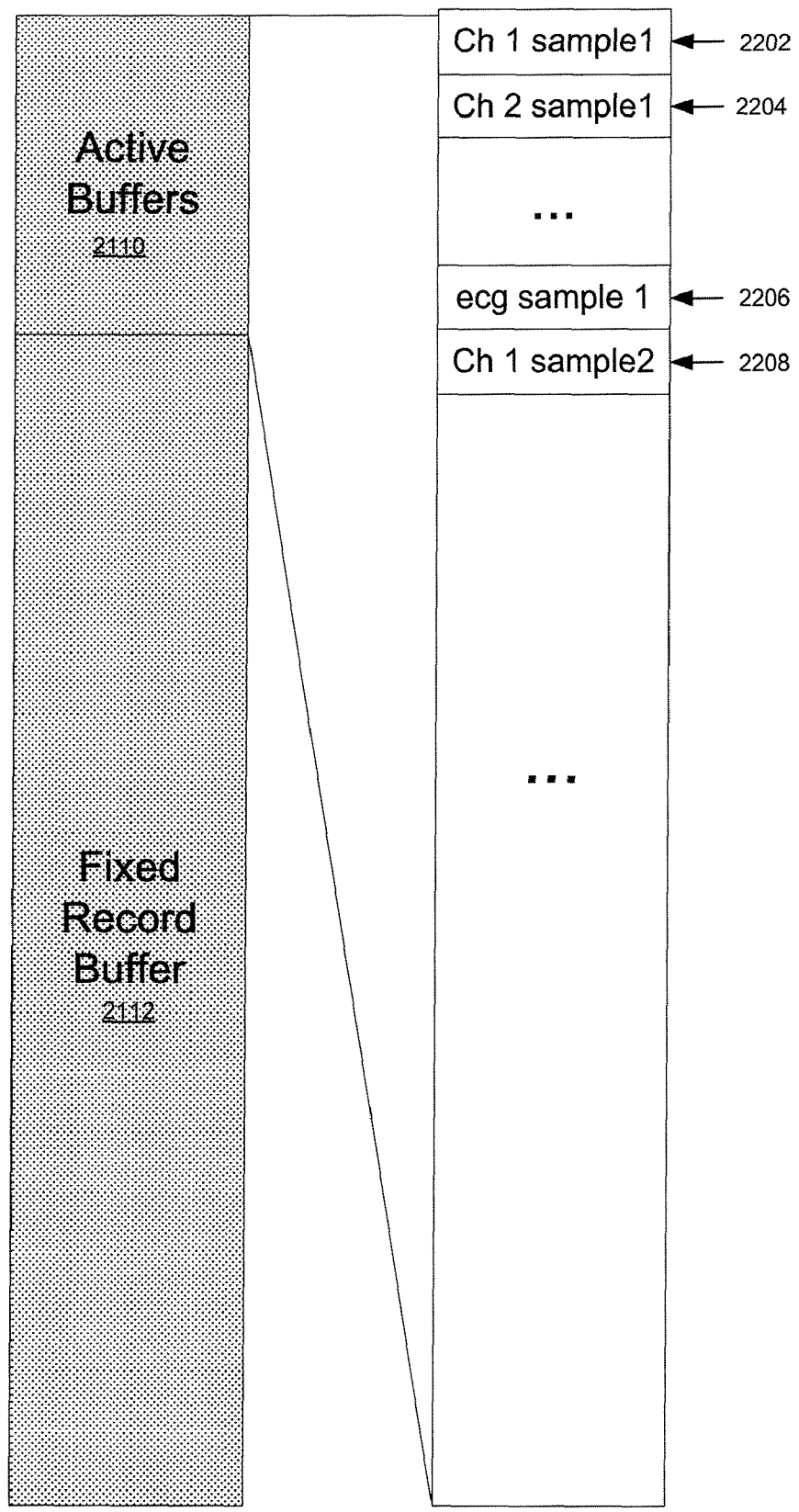
FIG. 8 illustrates an active buffer of the flexible memory management scheme in accordance with an aspect of the invention.

In FIG. 8, active buffers 2110 may store information received from various sense channels such as channel 1 sample 1 (2202), channel 2 sample 1 (2204), ecg sample 1 (2206), and channel 1 sample 2 (2208). The various sense channels may receive information from various portions of a patient's body. For example, channel 1 (2202) may be an EEG channel for storing information relating to a potential seizure; whereas, ecg sample 1 (2206) may receive information from an ECG sensor for evaluation of rate disturbances (e.g., bradycardia; tachycardia; asystole) as well as indications of cardiac ischemia.

Figure 9:
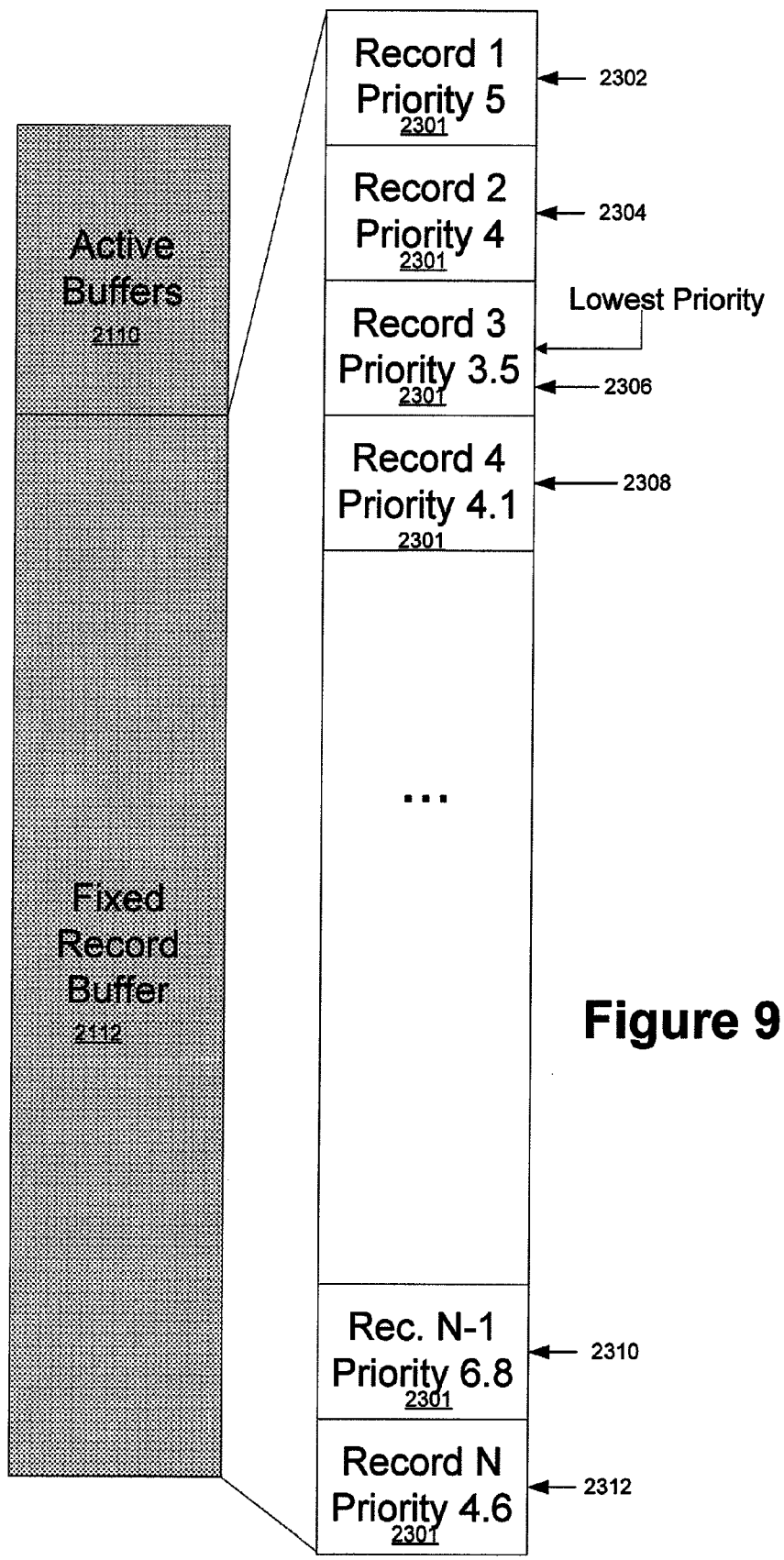
FIG. 9 illustrates a fixed record buffer of the flexible memory management scheme in accordance with an aspect of the invention.

The fixed record buffer 2112 as further illustrated in FIG. 9 may include a number of data records stored in various memory parts of the fixed memory area 2301. These memory segments in which the records are stored 2301 may not be of equal size and may not be contiguous.

As one skilled in the art will appreciate, to support various configurations which require different amounts of memory but still reduce waste as well as fragmentation and its associated complexity the invention disclosed herein describes a common blocksize. This may be calculated simply by using the GCD or "Greatest Common Divisor" of the total memory size associated with the configurations if appropriate total sizes are used. There may be other methods to calculate this blocksize which may be used instead and particularly if a large common divisor size cannot be found. The other methods may include attempts to optimize the trade-off between wasted space and fragmentation. "Fuzzy GCD" is an example of such an approach. Such calculation may be completed on an external device (where resources are rich at configuration time) and the resulting blocksize may just be communicated to the implantable device. The allocation and deallocation of blocks to recordings is also an aspect of block-based memory schemes and though the burden imposed on this may be reduced by having larger block-sizes it will still exist. To manage these aspects an allocation data structure (e.g. table or pointer based structure) may be used in the implantable medical device.

FIG. 9 illustrates the general concept of a number of records stored in the fixed memory area. The records include Record 1 2302, Record 2 2304, Record 3 2306, Record 4 2308, and Record N-1 2310. The number of N Records 2312 that may be stored in fixed record buffer 2112 may depend on the amount of memory allocated to fixed record buffer 2112. The Records (2302-2312) may be of different sizes as the amount of data recorded in each may be based on the configuration associated with the underlying event or trigger of each record.

As illustrated in FIG. 9, a priority may be determined for each of the Records (2302-2312). For instance, Record 1 2302 shows a Priority of 5, Record 2 2304 shows Priority of 4, Record 3 2306 shows a Priority of 3.5, Record 4 2308 shows a Priority of 4.1, Record N-1 2310 shows a Priority of 6.8, and Record N 2312 shows a Priority of 4.6. As new records are added and as older records are overwritten, priorities may be assigned and/or adjusted. The highest priority records may be saved in fixed record buffer 2112 and the lowest priority records may be overwritten. For instance, the highest priority record shown in FIG. 9 is Record N-1 2310 with a Priority of 6.8 and the lowest priority record is Record 3 2306 with a Priority of 3.5. If fixed record buffer 2112 is full, then Record 2306 the lowest priority may be the next record to be overwritten.

Figure 10:
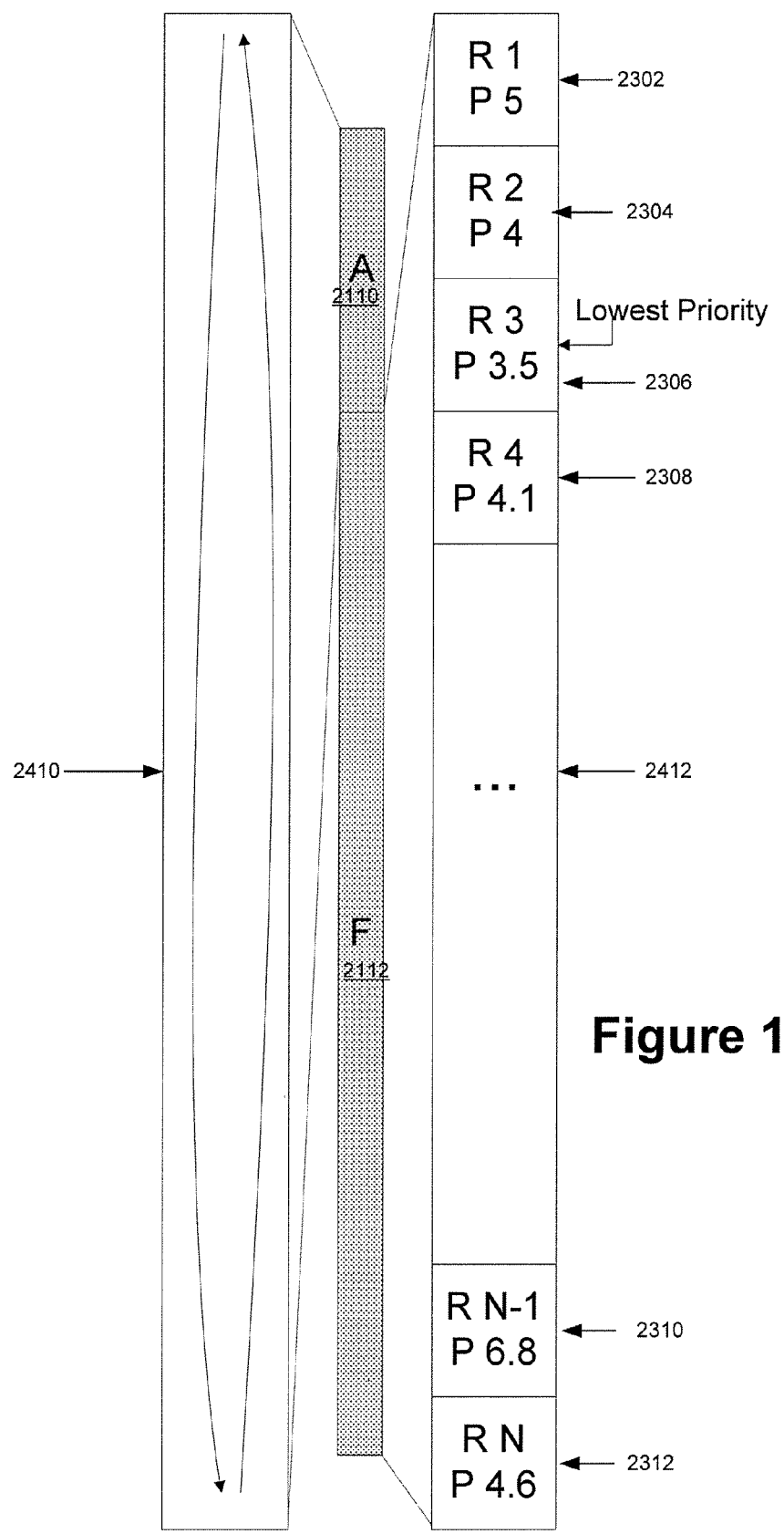
FIG. 10 illustrates a further example of a fixed record buffer of the flexible memory management scheme in accordance with an aspect of the invention.

FIG. 10 further illustrates the breakdown of fixed record buffer 2112 and active buffers 2110. In FIG. 10, the abbreviations of A for active buffers 2110 and F for fixed record buffer 2112 are used for illustrative purposes. As illustrated in FIG. 10, active buffers 2110 continues to record 2410 data before, after, and during event detection; whereas, fixed record buffer 2112 may store interleaved data 2412 copied to it from the active buffer after event detection. Those skilled in the art will realize that in other embodiments the data stored in fixed record buffer 2112 may not be interleaved.

Figure 11:
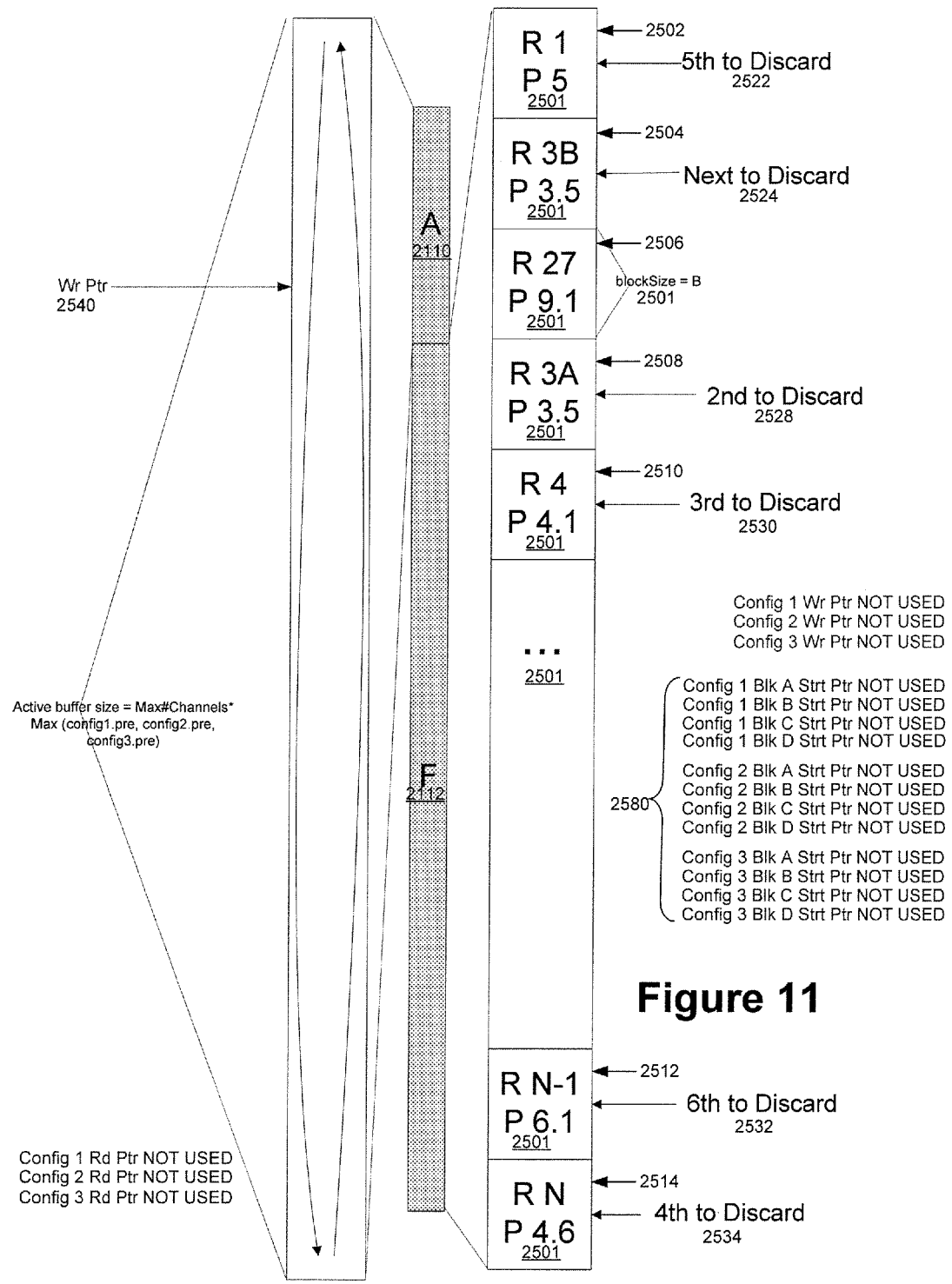
FIG. 11 illustrates equally sized memory block of the fixed record buffer of the flexible memory management scheme in accordance with an aspect of the invention.

FIG. 11 illustrates an aspect of the invention in which fixed record buffer 2112 is divided into equally sized memory blocks 2501 to store data Records 2502-2514. The use of equally sized memory blocks may allow for efficient storage of records. Use of equally sized memory blocks 2501 reduces possible gaps in memory usage and may eliminate the need to move data records back and forth to other locations in memory to maximize the amount of stored records.

As further illustrated in FIG. 11, each of the stored data records (2502-2514) has been assigned a priority and the priorities have been ranked. For example, the data records include the following information: data Record 1 2502 has a Priority of 5 and a ranking of $5^{th}$ to discard 2522, data Record 3B 2504 has a Priority of 3.5 and a ranking of Next to discard 2524, data Record 27 2506 has a Priority of 9.1 and has not yet received a ranking, data Record 3A 2508 has a Priority of 3.5 and a ranking of $2^{nd}$ to discard 2528, data Record 4 2510 has a Priority of 4.1 and a ranking of $3^{rd}$ to discard 2530, data Record N-1 2512 has a Priority of 6.1 and a ranking of $6^{th}$ to discard 2532, and data Record N 2514 has a Priority of 4.6 and a ranking of $4^{th}$ to discard 2534.

FIG. 11 also illustrates three different configurations 1, 2, and 3 that may be used to detect events in accordance with at least one aspect of the invention. For example configuration 1 may represent an event such as a cardiac event. Moreover, configuration 2 may represent a seizure event and configuration 3 may represent a manual event such as a patient initiated button press. Each of the configurations may utilize pointers to keep track of data that is being written to or read from memory blocks 2501. For instance, a write pointer 2540 is shown at a particular location in active buffers 2110. The write pointer 2540 may indicate the starting position and/or location of where additional data that may be written to located in active buffers 2110.

In FIG. 11, an event is not currently detected so pointers such as those used in copying data from the active to the fixed buffer area as shown in FIG. 11 may not be currently utilized. Furthermore, as illustrated in FIG. 11 each of the configurations maybe assigned a different number of memory blocks to store data associated with that particular configuration. This allows them to support varying amounts of data with a common block-size divisor. Note that recording 3 is using both block 2504 and block 2508 which may be separated by one or more blocks from another recording as shown with 2506. Moreover, each configuration may have Start pointers such as pointers 2580 to be used with that configuration. Finally, FIG. 11 also indicates that active buffers 2110 may be sized in accordance with a formula such as:

Active Buffer Size=(Maximum number of channels)* (Maximum Pre-event time)*(Sample rate).

Where Maximum Pre-event Time is in seconds and Sample rate is in words per second.

Figure 12:
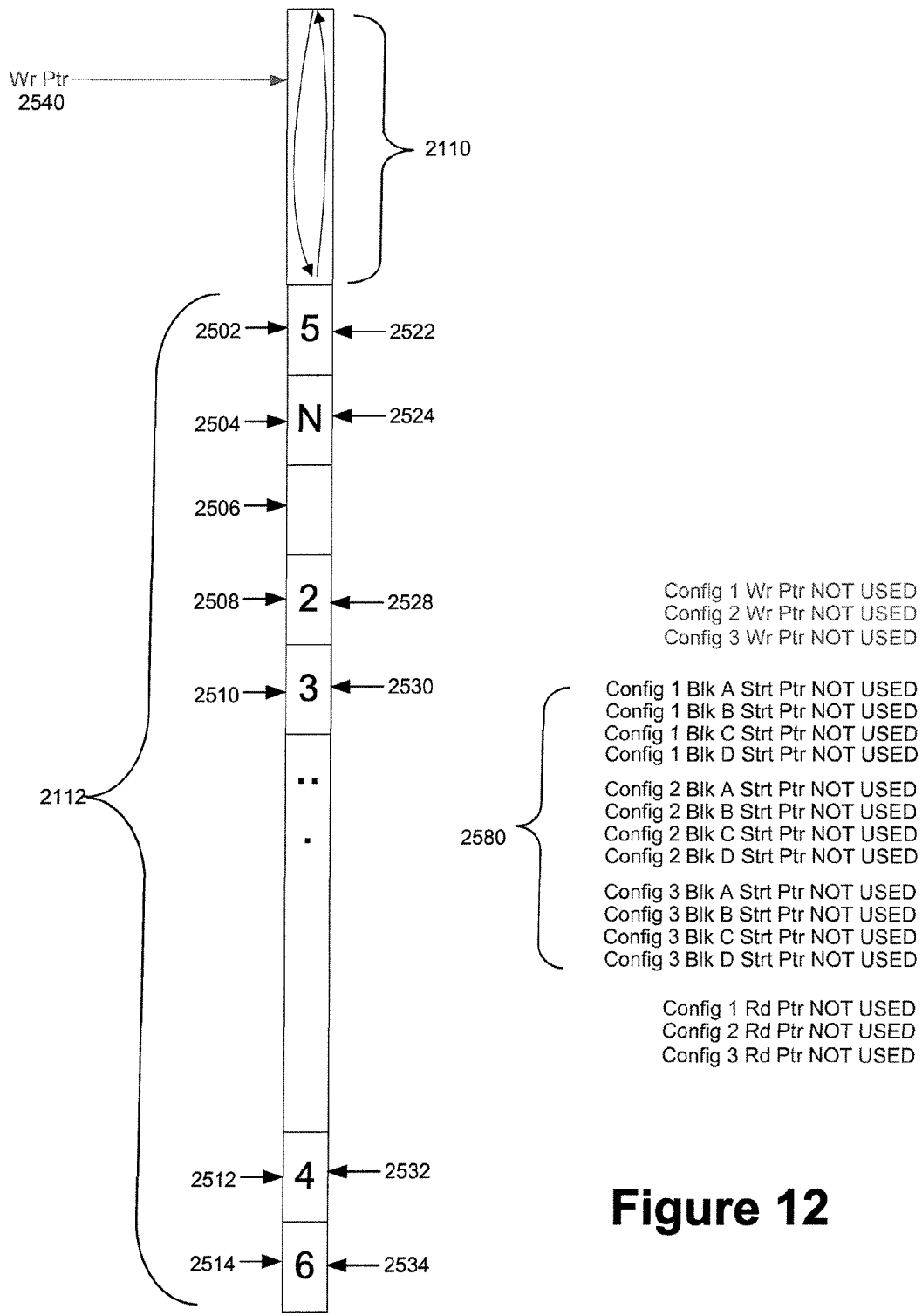
FIG. 12 illustrates another embodiment of the equally sized memory block of the fixed record buffer of the flexible memory management in accordance with an aspect of the invention.

FIG. 12 illustrates some of the information displayed in FIG. 11 but using an abbreviated form for clarity. For example, the ranking of $5^{th}$ block to discard 2522 has been abbreviated to 5 in FIG. 11. As one skilled in the art will realize various prioritization and retention schemes are possible including those which free memory on a record by record rather than block by block level. An examination of FIG. 11 and FIG. 12 together may clarify the abbreviations used in FIG. 12. Moreover, like numerals have been utilized to refer to like items discussed throughout the detailed description.

Figure 13:
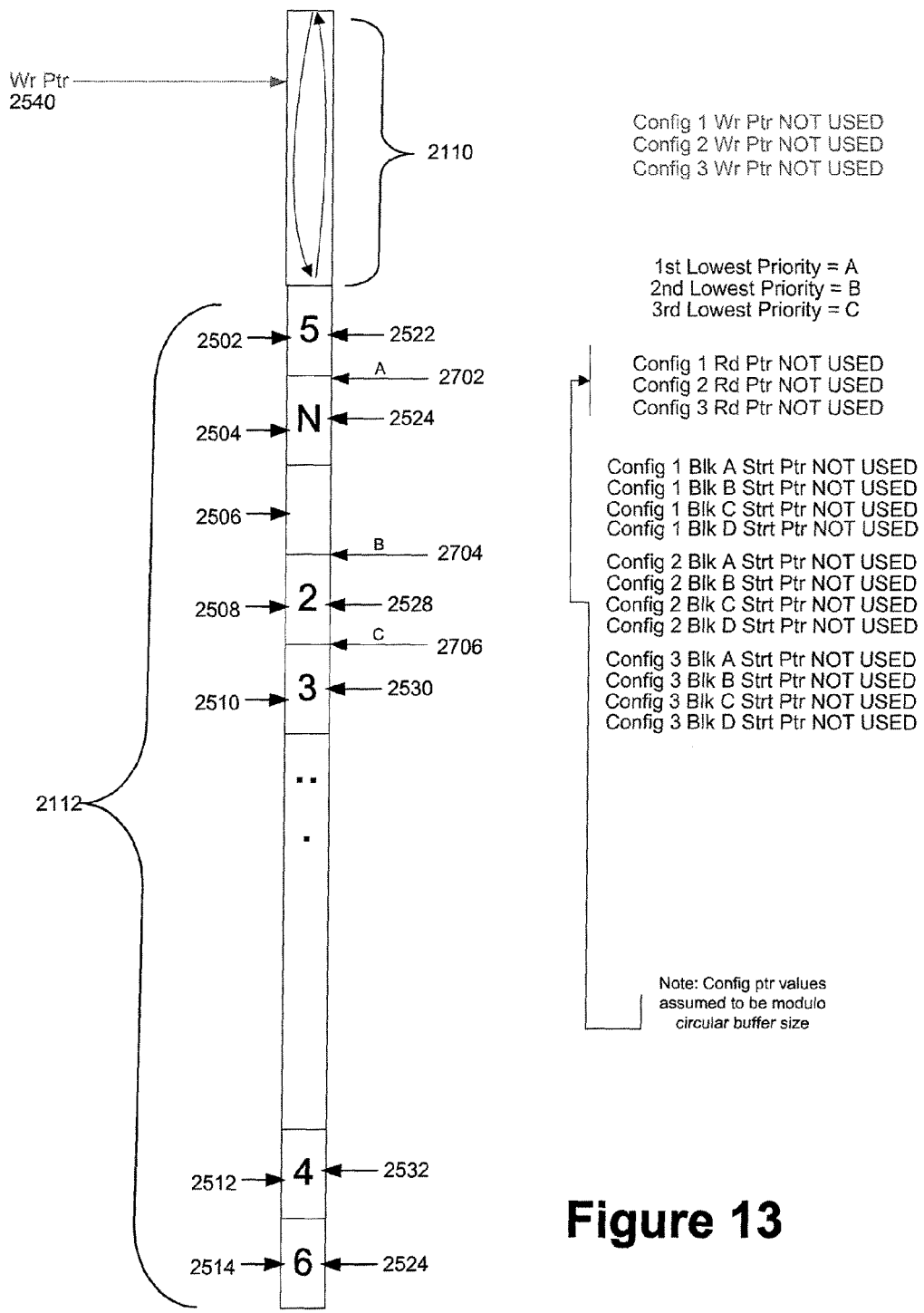
FIG. 13 illustrates the flexible memory management scheme at an instance before detection of an event in accordance with an aspect of the invention.

FIG. 13 illustrates an aspect of the invention at an instance before an event is detected in a first configuration. In FIG. 13, three pointers A (2702), B (2704), and C (2706) are located at the beginning of the lowest priority records. For instance, pointer A (2702) is positioned at the beginning of a memory block 2501 (more specifically memory block memory block 2504 containing part of a Record "3B") and having a priority of next to discard 2524. Pointer B 2704 is positioned at the beginning of a second memory block 2501 (more specifically memory block 2508 containing part of a Record "3 A") and having a $2^{nd}$ to discard priority 2528. Pointer C (2706) is positioned at the beginning of a third memory block 2501 (more specifically memory block 2510 containing a Record "4 " and having a priority of $3^{rd}$ to discard 2530. As those skilled in the art will realize, the data records 2504, 2508, and 2510 will remain stored until new events are received and additional storage space is needed.

Figure 14:
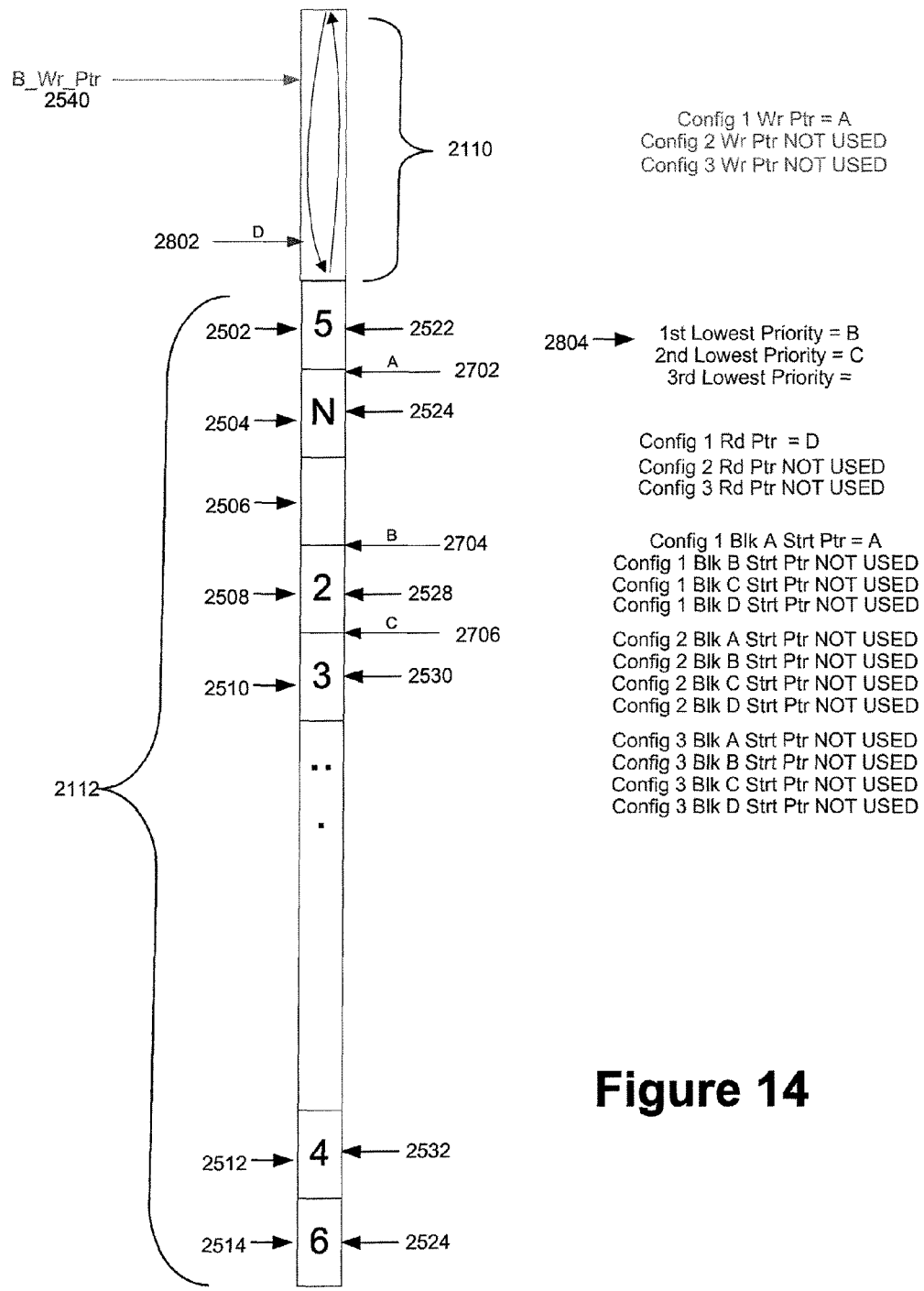
FIG. 14 illustrates the flexible memory management scheme at a first instance of an event in accordance with an aspect of the invention.

FIG. 14 illustrates a first instance of an event on a first configuration. In FIG. 14, based on the type of received event, data starting at pointer D 2802 may be copied from active buffers 2110 to fixed record buffer 2112. In particular, based on the received event it may be determined that an amount of pre-event data starting at pointer D 2802 will be transferred to fixed record buffer 2112 starting at pointer A (2702). For example, if the event was a seizure event and the pre-event recording time was two minutes then pointer D 2802 represents the starting location of pre-event information of interest to the physician or caregiver.

Therefore, as illustrated in FIG. 14, in accordance with an aspect of the invention, data may be read from active buffers 2110 starting at pointer D 2802 and written to fixed record buffer 2112 starting at pointer A 2702. As new data is being written to fixed record buffer 2112, priorities of or affecting the next blocks of data to be overwritten may be updated. As shown in FIG. 14, priorities 2804 are updated so that the lowest priority indicated is located starting at pointer B (2704).

Figure 15:
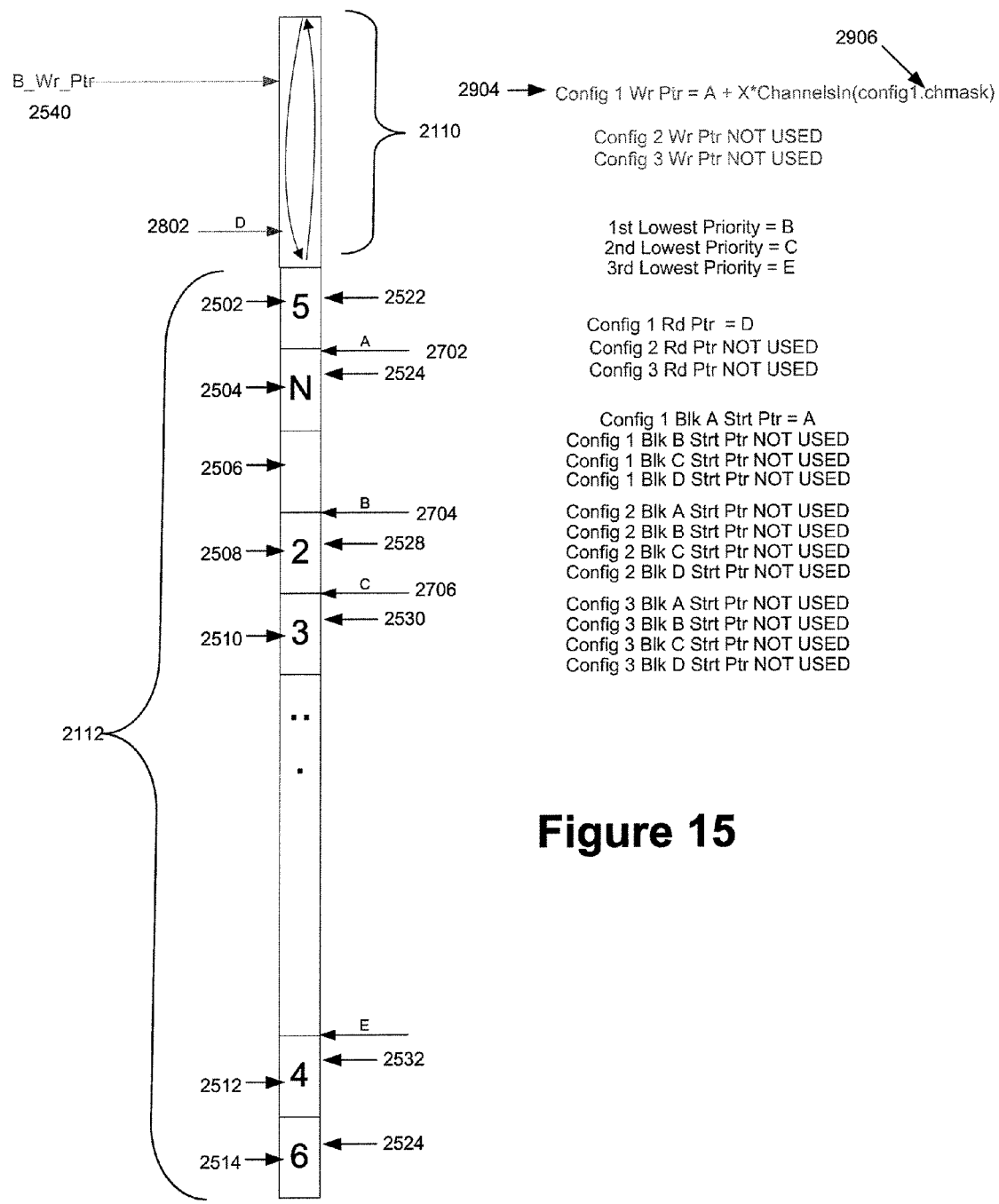
FIG. 15 illustrates the flexible memory management scheme at a number of samples after event detection in accordance with an aspect of the invention.

FIG. 15 illustrates an aspect of the invention at a number of x samples after the event has been detected. In FIG. 15, as illustrated at 2902, the new reading location for the read pointer may be determined from the original location of pointer D as advanced in the direction of newer data in a manner proportional to x (e.g. as would have been achieved by moving in lock-step with the write pointer for each of the x samples). Thus the new location of pointer D and associated reading will be at a different location in active buffer 2110. Moreover, as FIG. 15 illustrates in an aspect of the invention, the new writing location may be determined from the original location of pointer A plus x times the number of channels that are being saved (2904). The channel masks 2906 for the first configuration may assist in determining how many channels need to be written. As one skilled in the art will recognize, the calculation of the location of pointers like the read and write pointers just discussed may involve the use of other factors (e.g. related to common compression that might be used in the active or fixed buffers) as well.

In an aspect of the invention, each of the configurations allows for the saving of different channels and combination of channels. Though the superset of this information is recorded in active buffers 2110, only the information particular to the configuration is saved to fixed record memory 2112.

Figure 16:
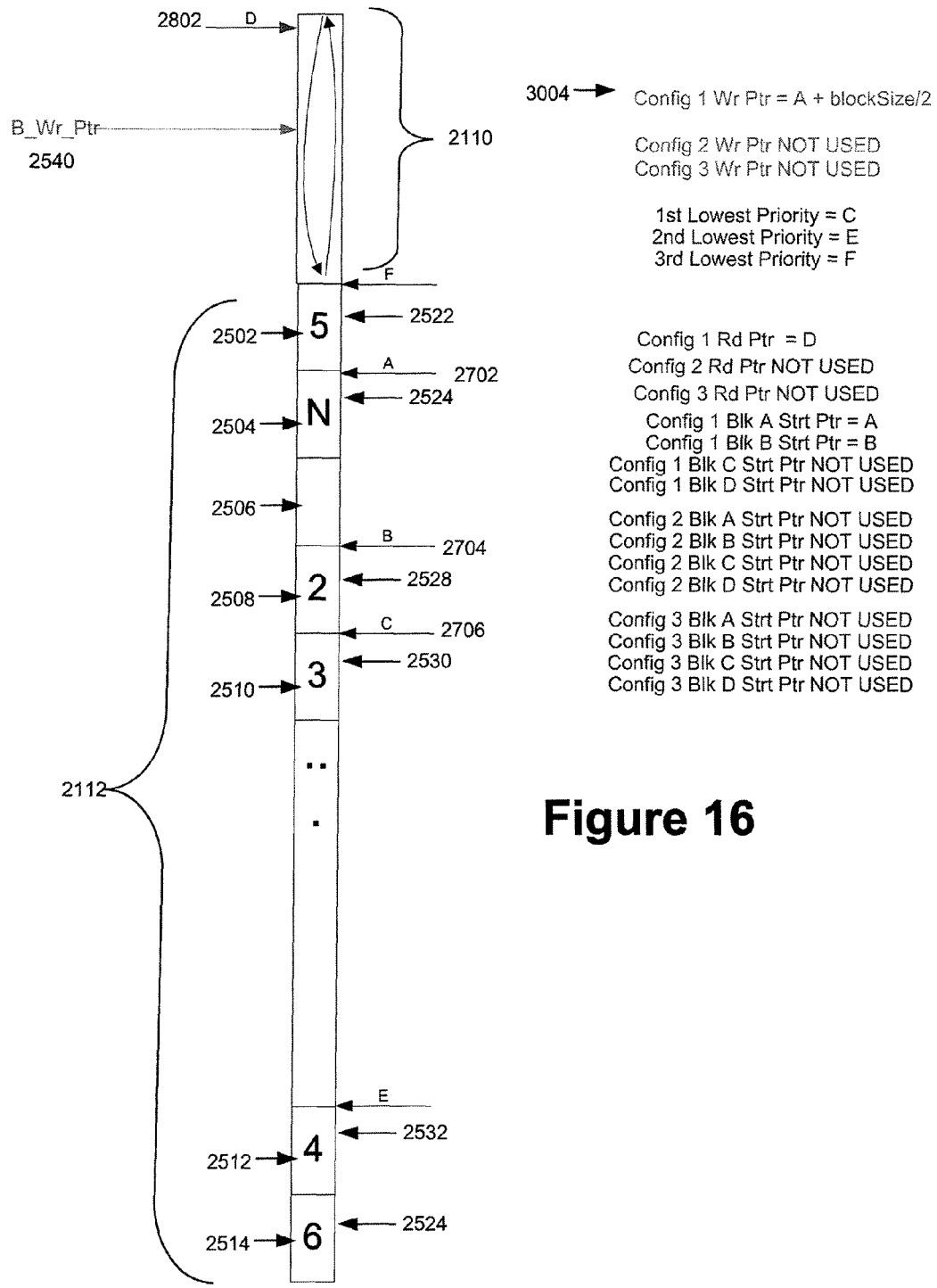
FIG. 16 illustrates the flexible memory management scheme where a sequence has advanced to a halfway point of a memory block in accordance with an aspect of the invention.

FIG. 16 illustrates a further example where the sequence has advanced to a point halfway through memory block 2501. In particular, the reading location for the read pointer has advanced as described previously from the original position of pointer D to the new position of D in the active buffer. Moreover, as FIG. 16 illustrates in an aspect of the invention, the new writing location may be determined 3004 from the original location of pointer A plus (blocksize/2) (3004).

Figure 17:
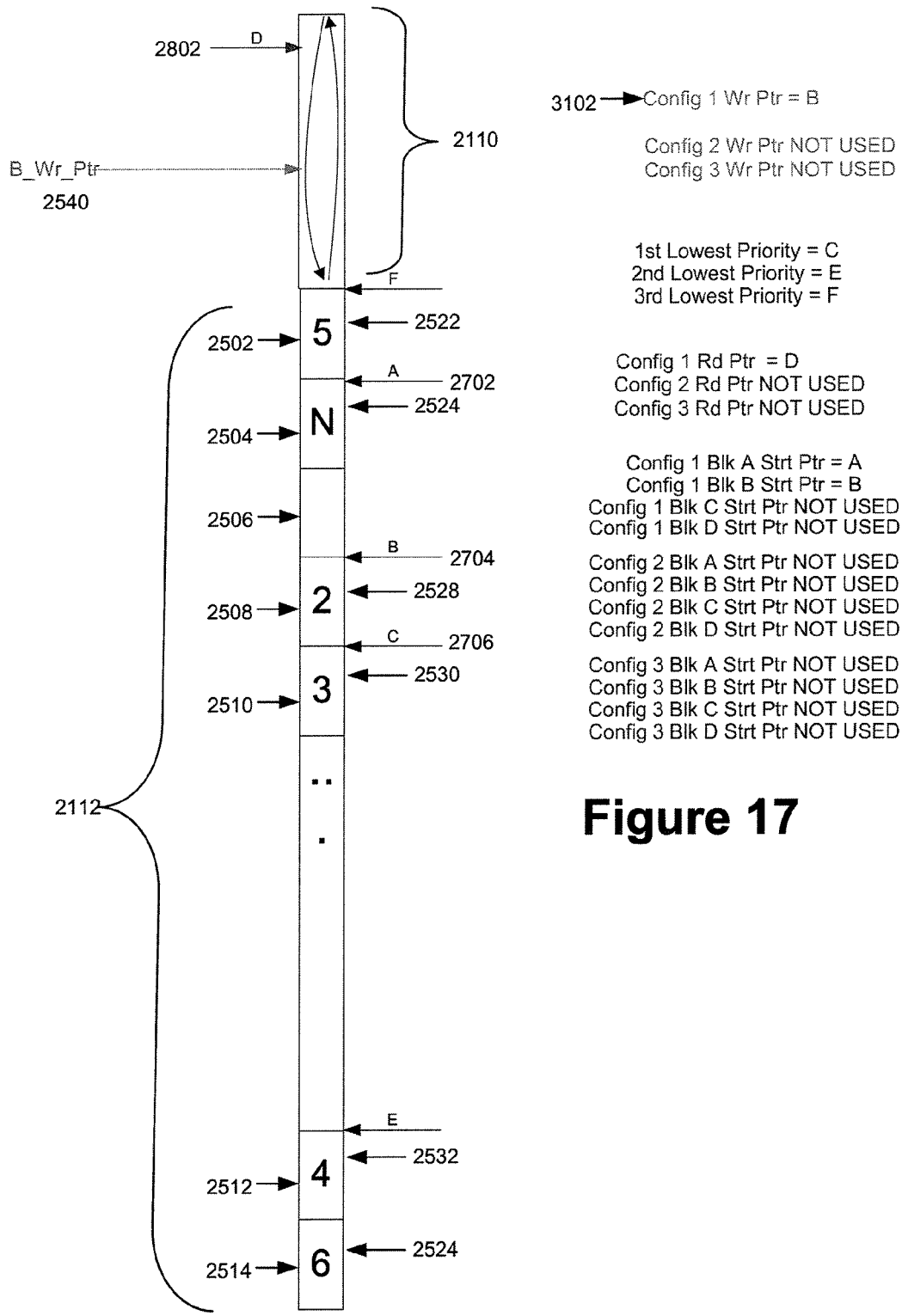
FIG. 17 illustrates the saving of data to additional blocks of memory of the flexible memory management scheme in accordance with an aspect of the invention.

FIG. 17 illustrates a further example where the first block of a first configuration has been written to and a second block such as a block B will be written to 3102. As shown in FIG. 17, block B will be written over the next lowest priority which is B 2704.

In another aspect of the invention, a second event may be detected while the first event is being recorded. For example, if the first event was an ISDA detection trigger and the second event was the end of a seizure cluster. (The ISDA trigger may be considered more important than the end of seizure event. In this case, at some time the second loop recording may get overwritten before the first if memory is filled and a block is needed for a new loop recording).

Figure 18:
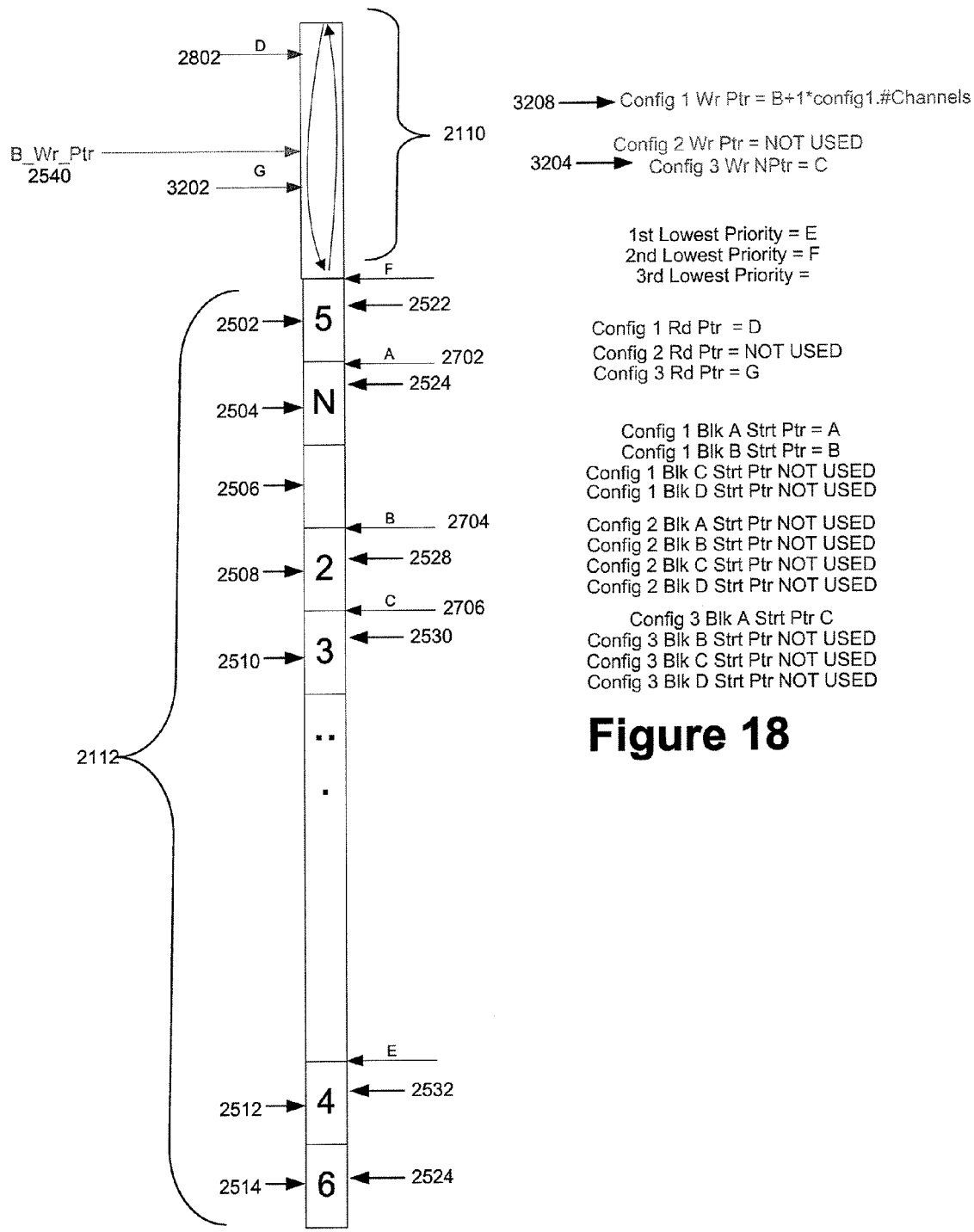
FIG. 18 illustrates the detection of a second event of the flexible memory management scheme in accordance with an aspect of the invention.

For example, FIG. 18 shows a second event detected on a third configuration channel. The active buffers 2110 of FIG. 18 show two read pointers: reader pointer D 2802 and reader pointer G 3202. Reader pointer G 3202 may represent a location at the beginning of the pre-event recording to be saved for analysis. Furthermore, a write pointer 3204 for the third configuration channel is shown in FIG. 18. The write pointer may begin recording at pointer C 2706 located at the beginning of data record 2510. Therefore, as shown two different configurations may be loop recorded simultaneously.

Figure 19:
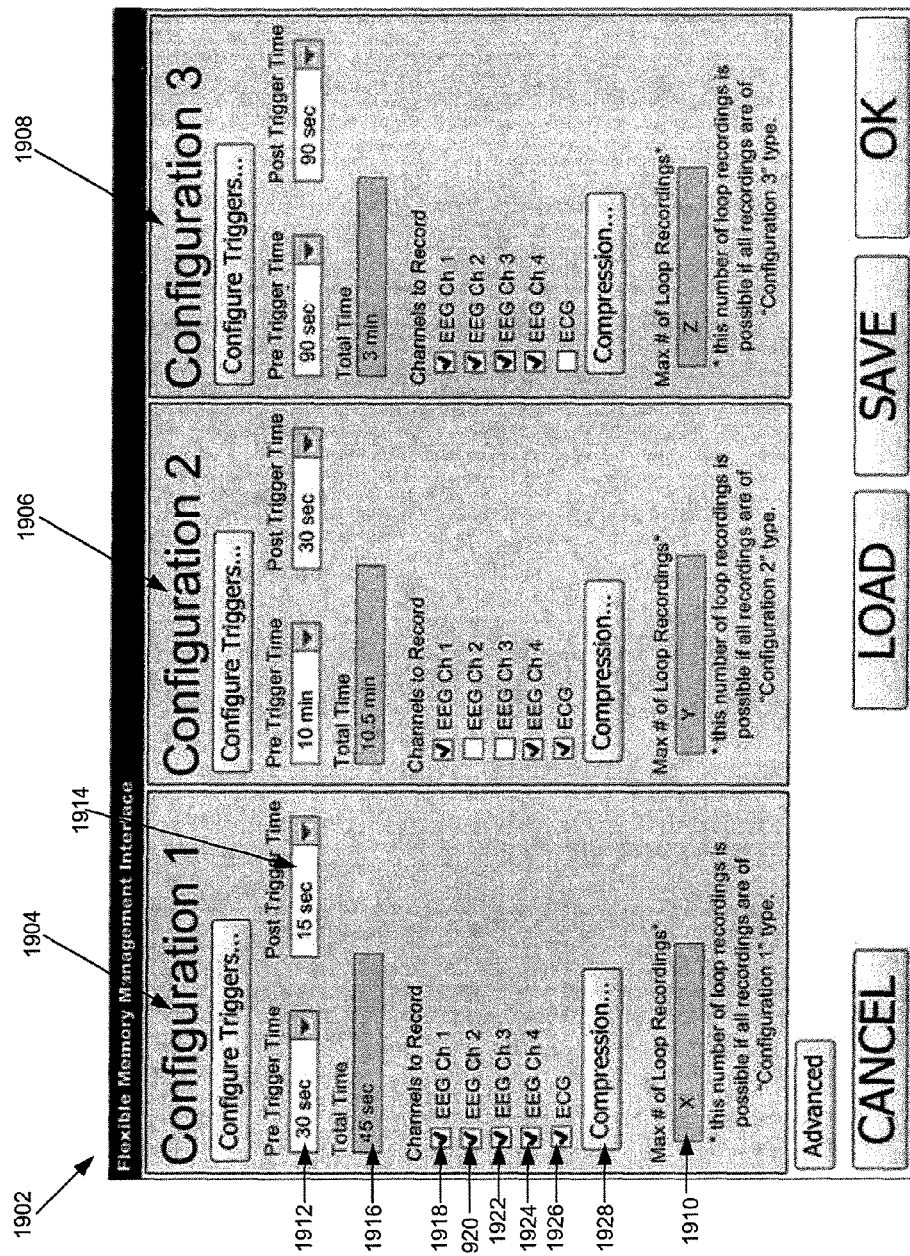
FIG. 19 shows a graphical user interface that may be used in accordance with an aspect of the invention.

FIG. 19 shows a graphical user interface 1902 that represents a multitude of configurations that may used in accordance with an aspect of the invention. The graphical user interface 1902 illustrates three separate instances of a loop recording algorithm, each operating independently. The three separate instances include configuration "1" 1904, configuration "2" 1906, and configuration "3" 1908. Each of the configurations may contain similar selection criteria for determining a number of loop recordings to be recorded for each configuration.

In one aspect of the invention, a device having a fixed amount of memory may use graphical interface 1902 to determine a maximum number 1910 that may be stored for each configuration. For example, an implantable device may have a total of 2 MB of memory to store data. A certain portion of the memory may be needed to store or log events in an event log. This space may be in the order of 200 K of memory. The remaining 1.8 MB of memory may be allocated for storing waveform data associated with the events. As those skilled in the art will realize, a device such as an implantable device may have more or less memory for use in storing waveform and event data. The above example in only one illustrative example and is not intended to limit the described aspects of the invention.

In an aspect of the invention, different configurations such as configuration "1" 1904, configuration "2" 1906, and configuration "3" 1908 may each be allotted a different amount of memory in which to store waveform and event data. As one skilled in the art will realize, the allotment need not be predetermined or static, but rather may be updated based on a priority scheme as described previously. The selected criteria for each configuration may determine the maximum number of loop recording that may be saved for each configuration.

The selection of criteria for an exemplary configuration is illustrated in the following discussion. In FIG. 19, configuration "1" 1904 may include a pre-trigger time 1912, a post-trigger time 1914, and a total time 1916. For example, the selected pre-trigger time 1912 may be 30 seconds, whereas, the selected post-trigger time 1914 may be 15 seconds. The total time 1916 may be the result of the pre-trigger time 1912 and the post-trigger time 1914, forty-five seconds. Those skilled in the art will realize that the amount of time selected for the pre-trigger time 1912 and post-trigger time 1914 may depend on the frequency of events that a particular user may be experiencing or other factors considered by the user. In addition, a physician or other caregiver may set the pre-trigger time 1912 and post-trigger time 1914 based on the type of event which they expect to record in order to produce useful data for analysis. One skilled in the art will realize that various other types of memory allocation other than pre-trigger and post-trigger times are also possible with this scheme (e.g. one may chose instead to store only some time around wherever the peak occurs during some recording period as described in concurrently filed patent application entitled "Peak Data Retention of Signal Data in an Implantable Medical Device" 11/380586 the entire disclosure of which is hereby incorporated by reference).

In FIG. 19, various channels may be enabled to collect event information. For instance, a physician or caregiver may select to record information from EEG channel "1" 1918, EEG channel "2" 1920, EEG channel "3" 1922, and EEG channel "4" 1924. In addition, data relating to an ECG channel 1926 may also be recorded. One skilled in the art will realize that other types, numbers and combinations of channels may be used in other embodiments. The number of channels selected may affect the maximum number of loop recording 1916 that may be saved. In particular, increasing the number of enabled channels to be recorded decreases the maximum number of loop recordings 1910 that that may be saved in the device. As those skilled in the art will realize, by manipulating the pre-trigger time 1912, post-trigger time 1914, the enabled channels (1918-1926), and recording details like compression, a physician or caregiver may obtain a particular number of loop recording to analyze.

Moreover, data compression may be used to store an additional number of loop recording or a longer record time for the same number of loop recording. In FIG. 19, a user or caregiver may select that a data compression scheme be utilized. The compression scheme may be fixed ratio data compression for multiple types of physiologic signal channels (both EEG and ECG). For example, an EEG compression ratio may be selected by a physician or caregiver. Because an objective of loop recording may be to provide to physician or caregiver with waveforms for visual analysis, the data compression may be lossy, as long as it does not distort the signal to the point where the physician or caregiver is unable to make an accurate diagnosis.

In an aspect of the invention, four EEG channels are available (1918-1924) and enabled for recording (FIG. 12). In an embodiment, all enabled EEG channels (1918-1924) may have the same compression settings. For EEG (or other signal) compression, the ratios may include the following compression ratios as shown in Table 1. Table 1 also includes a brief description of the compression technique that may be implemented to achieve the selected compression ratio.

TABLE 1

| EEG Compression | |
| --- | --- |
| 1:1 | No compression |
| 2:1 | Delta companding |
| 4:1 | NTP, delta companding |
| 8:1 | NTP, NTP, delta companding |
| 16:1 | NTP, NTP, range companding, D/R |

The EEG compression rations may be selected upon activation of the compression activation button 1928.

In another aspect of the invention, ECG channel 1926 may also be available for compression. In an embodiment, ECG channel 1926 may be compressed using ECG compression ratios as illustrated in Table 2. Table 2 also includes a brief description of the compression technique that may be implemented to achieve the selected compression ratio.

TABLE 2

| ECG Compression | |
| --- | --- |
| 1:1 | No compression |
| 2:1 | Delta companding |
| 4:1 | NTP, delta companding |

The ECG compression ratios may be selected upon activation of the compression activation button 1928. As those skilled in the art will realize, other compression ratios for the EEG, ECG, or other physiologic signal channels or any combination thereof may be utilized as the physician or clinician may desire to set compression parameters not listed in these tables. In the case of a non-default choice, an advanced compression settings widget (e.g. button or tab; not shown) may be available to the user allowing greater flexibility in the setting of compression ratios. As an alternative, all compression settings may be placed in an advanced dialog box or other interface to simplify the main loop recording user interface.

Thus, various embodiments of the invention have been disclosed. One skilled in the art will appreciate that the above teachings may be practiced with embodiments other than those disclosed. The disclosed embodiments are presented for purposes of illustration and not limitation, and the inventions are limited only by the claims that follow.

What is claimed:

1. A method of handling recordings in an implantable device, the method comprising:
    (a) prioritizing data using a priority index, the priority index based on a severity level function, the data stored in data blocks of a fixed buffer;
    (b) initiating a first recording in an active buffer, the first recording storing pre-event data associated from a signal set;
    (c) detecting a first event and a type of the first event;

(d) determining a sensing configuration based on the type of the first event, the configuration specifying a time duration having a pre-event time and a post-event time that indicates a total amount of time to record data of the first event;
(e) copying the pre-event data associated with the first event beginning at the pre-event time into a data block of the fixed buffer having lowest priority data as determined in (a);
(f) saving post-event data associated with the first event until the post-event time in the data block of the fixed buffer including the pre-event data; and
(g) re-prioritizing data using the priority index, the data stored in data blocks of the fixed buffer.

2. The method of claim 1, wherein the active buffer comprises a circular buffer.

3. The method of claim 1, wherein the configuration specifies at least one of a plurality of channels to record based on the type of the first event.

4. The method of claim 1, wherein the active buffer is sized based on equation Active Buffer Size=(Maximum number of channels)*(Maximum Pre-event time).

5. The method of claim 1, wherein data stored in the fixed buffer is interleaved.

6. The method of claim 1, further comprising (h) initiating a second recording in the active buffer, the second recording storing pre-event data from a second signal set.

7. The method of claim 6, further comprising:
(i) detecting a second event;
(j) copying pre-event data associated with the second event into a data block having the second lowest priority data as determined in (g); and
(k) saving post-event data associated with the second event in the data block of the fixed buffer including the second pre-event data.

8. The method of claim 7, wherein the second event comprises a second trigger, the second trigger including an electrocardiogram trigger.

9. The method of claim 7, wherein the second event comprises a second trigger, the second trigger including a seizure detection algorithm trigger.

10. The method of claim 7, wherein the second event comprises a second trigger, the second trigger including a manual trigger.

11. The method of claim 1, wherein the first event comprises a first trigger, the first trigger including an electrocardiogram trigger.

12. The method of claim 1, wherein the first event comprises a first trigger, the first trigger including a seizure detection algorithm trigger.

13. The method of claim 1, wherein the first event comprises a first trigger, the first trigger including a manual trigger.

14. An implantable medical device comprising:
(a) a first monitoring element that receives a first signal set associated with a physiologic condition;
(b) a second monitoring element that receives a second signal set;
(c) a storage medium; and
(d) a processing module coupled to the storage medium and programmed with computer-executable instructions for performing:
(i) prioritizing data using a priority index, the priority index based on a severity level function, the data stored in data blocks of a fixed buffer;
(ii) initiating a first recording in an active buffer, the first recording storing pre-event data associated from a signal set;
(iii) detecting a first event and a type of the first event;
(iv) determining a sensing configuration based on the type of the first event, the configuration specifying a time duration having a pre-event time and a post-event time that indicates a total amount of time to record data of the first event;
(v) copying the pre-event data associated with the first event beginning at the pre-event time into a data block of the fixed buffer having lowest priority data as determined in (i);
(vi) saving post-event data associated with the first event until the post-event time in the data block of the fixed buffer including the pre-event data; and
(vii) re-prioritizing data using a priority index, the data stored in data blocks of the fixed buffer.

15. The device of claim 14, wherein the active buffer comprises a circular buffer.

16. The device of claim 14, further comprising (viii) initiating a second recording in the active buffer, the second recording storing pre-event data from a second signal set.

17. The device of claim 16, further comprising:
(ix) detecting a second event;
(x) copying pre-event data associated with the second event into a data block having the second lowest priority data a determined in (vii); and
(xi) saving post-event data associated with the second event in the data block of the fixed buffer including the second pre-event data of the second recording.

* * * * *